US010878219B2

(12) United States Patent
Zhou et al.

(10) Patent No.: US 10,878,219 B2
(45) Date of Patent: Dec. 29, 2020

(54) METHOD AND SYSTEM FOR ARTIFICIAL INTELLIGENCE BASED MEDICAL IMAGE SEGMENTATION

(71) Applicant: Siemens Healthcare GmbH, Erlangen (DE)

(72) Inventors: Shaohua Kevin Zhou, Plainsboro, NJ (US); Mingqing Chen, Plainsboro, NJ (US); Hui Ding, College Park, MD (US); Bogdan Georgescu, Plainsboro, NJ (US); Mehmet Akif Gulsun, Princeton, NJ (US); Tae Soo Kim, Baltimore, MD (US); Atilla Peter Kiraly, San Jose, CA (US); Xiaoguang Lu, West Windsor, NJ (US); Jin-hyeong Park, Princeton, NJ (US); Puneet Sharma, Princeton Junction, NJ (US); Shanhui Sun, Princeton, NJ (US); Daguang Xu, Princeton, NJ (US); Zhoubing Xu, Plainsboro, NJ (US); Yefeng Zheng, Princeton Junction, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 73 days.

(21) Appl. No.: 16/094,900

(22) PCT Filed: Jul. 19, 2017

(86) PCT No.: PCT/EP2017/068181
§ 371 (c)(1),
(2) Date: Oct. 19, 2018

(87) PCT Pub. No.: WO2018/015414
PCT Pub. Date: Jan. 25, 2018

(65) Prior Publication Data
US 2019/0205606 A1 Jul. 4, 2019

Related U.S. Application Data

(60) Provisional application No. 62/414,913, filed on Oct. 31, 2016, provisional application No. 62/365,032, filed on Jul. 21, 2016.

(51) Int. Cl.
*G06K 9/00* (2006.01)
*G06K 9/46* (2006.01)
(Continued)

(52) U.S. Cl.
CPC ......... *G06K 9/0014* (2013.01); *G06K 9/4628* (2013.01); *G06N 3/0445* (2013.01);
(Continued)

(58) Field of Classification Search
CPC .. G06K 9/0014; G06K 9/4628; G06K 9/6209; G06N 3/0445; G06N 3/0454; G06N 3/084; G06T 7/11; G16H 30/40
See application file for complete search history.

(56) References Cited

U.S. PATENT DOCUMENTS

2011/0007954 A1  1/2011  Suehling et al.
2018/0300882 A1* 10/2018  Kim ................. G06K 9/00201

FOREIGN PATENT DOCUMENTS

EP      2863360 A1    4/2015

OTHER PUBLICATIONS

Long, J., Shelhamer, E., Darrell, T.: Fully convolutional networks for semantic segmentation. In: Proc. CVPR (2015).
(Continued)

*Primary Examiner* — Charles T Shedrick

(57) ABSTRACT

Methods and systems for artificial intelligence based medical image segmentation are disclosed. In a method for
(Continued)

autonomous artificial intelligence based medical image segmentation, a medical image of a patient is received. A current segmentation context is automatically determined based on the medical image and at least one segmentation algorithm is automatically selected from a plurality of segmentation algorithms based on the current segmentation context. A target anatomical structure is segmented in the medical image using the selected at least one segmentation algorithm.

21 Claims, 26 Drawing Sheets

(51) Int. Cl.
*G06T 7/11* (2017.01)
*G06N 3/04* (2006.01)
*G06N 3/08* (2006.01)
*G06K 9/62* (2006.01)
*G16H 30/40* (2018.01)

(52) U.S. Cl.
CPC ........... *G06N 3/0454* (2013.01); *G06N 3/084* (2013.01); *G06T 7/11* (2017.01); *G06K 9/6209* (2013.01); *G16H 30/40* (2018.01)

(56) References Cited

OTHER PUBLICATIONS

Y Zheng, A Barbu, B Georgescu, M Scheuering, D Comaniciu, "Four-chamber heart modeling and automatic segmentation for 3-D cardiac CT vols. using marginal space learning and steerable features," IEEE Transactions on Medical Imaging, 27 (11), 1668-1681, 2008.

T. F. Cootes and C.J. Taylor and D.H. Cooper and J. Graham. "Active shape models—their training and application". Computer Vision and Image Understanding (61): 38-59, 1995.

Ghesu, Florin C., et al. "An artificial agent for anatomical landmark detection in medical images." International Conference on Medical Image Computing and Computer-Assisted Intervention. Springer International Publishing, 2016.

S. K. Zhou and D. Comaniciu, "Shape regression machine," Proc. Information Processing in Medical Imaging, 2007, pp. 13-25.

Alvarez, J., Peterson, L. DecomposeMe: Simplifying ConvNets for end-to-end learning. CoRR 2016.

Yani Ioannou, Duncan P. Roertson, Antonio Criminisi. Deep Roots: Improving CNN Efficiency with Hierarchical Filter Groups. CoRR, 2016.

Viola, Paul, and Michael Jones. "Fast and robust classification using asymmetric adaboost and a detector cascade." Advances in Neural Information Processing System 14 (2001).

Tu, Zhuowen. "Probabilistic boosting-tree: Learning discriminative models for classification, recognition, and clustering." Tenth IEEE International Conference on Computer Vision (ICCV'05) vol. 1. vol. 2. IEEE, 2005.

Y. Tsadok, Y. Petranka, S. Sarvarib, T. Edvardsenb, and D. Adama, "Automatic segmentation of cardiac MRI cines validated for long axis views," Computerized Medical Imaging and Graphics, 37: 500-511, 2013.

V. Badrinarayanan, A. Kendall, and R. Cipolla, SegNet: A Deep Convolutional Encoder-Decoder Architecture for Image Segmentation, CoRR, abs/1511.00561, 2015.

International Search Report annd Written Opinion dated Sep. 28, 2017 in corresponding International Application No. PCT/EP207/068181.

Roth Holger R et al: "DeepOrgan: Multi-level Deep Convolutional Networks for Automated Pancreas Segmentation"; Nov. 18, 2015; Network and Parallel Computing; [Lecture Notes in Computer Science; Lect.Notes Computer]; Springer International Publishing; Cham; pp. 556-564.

Yann Lecun et al: "Deep learning"; Nature; May 27, 2015; vol. 521 No. 7553; pp. 436-444.

* cited by examiner

METHOD AND SYSTEM FOR ARTIFICIAL INTELLIGENCE BASED MEDICAL IMAGE SEGMENTATION

This application claims the benefit of U.S. Provisional Application No. 62/365,032, filed Jul. 21, 2016, and U.S. Provisional Application No. 62/414,913, filed Oct. 31, 2016, the disclosures of which are herein incorporated by reference in its entirety.

BACKGROUND OF THE INVENTION

The present invention relates to computer-based segmentation of medical images, and more particularly to computer-based artificial intelligence based segmentation of target structures in medical images.

Medical image segmentation is an important technology that supports the entire clinical imaging workflow from diagnosis, patient stratification, therapy planning, intervention, and follow-up. Medical image segmentation refers to the detection of boundaries of structures, such as organs, vessels, different types of tissue, pathologies, medical devices, etc., in medical images of a patient. Automatic segmentation of anatomical objects is a prerequisite for many medical image analysis tasks, such as motion tracking, disease diagnosis, and quantification. Medical image registration is used in a large number of applications to detected various anatomical objects or other structures in various different medical imaging modalities, such as computed tomography (CT), magnetic resonance imaging (MRI), ultrasound, x-ray, DynaCT, positron emission tomography (PET), laparoscopic/endoscopic imaging, etc. In many applications, automatic medical image segmentation is challenging due to low contrast, image noise, or other imaging ambiguities. Due to the vast range of applications to which medical image segmentation can be applied, it is challenging to develop a general medical image segmentation method that works robustly for all uses.

BRIEF SUMMARY OF THE INVENTION

The present invention provides methods and systems for artificial intelligence based segmentation of medical images. Embodiments of the present invention provide multiple artificial intelligence based medical image segmentation methods, including multiple different deep learning based medical image segmentation methods. Embodiments of the present invention also provide a method and system for autonomous artificial intelligence based medical image segmentation in which a trained intelligent artificial agent performs intelligent automated recognition of segmentation tasks and intelligent automated selection and application of segmentation algorithms. This allows the intelligent artificial agent to be applied to intelligently perform various different segmentation tasks, including segmentation of different anatomical structures and segmentation in different medical imaging modalities.

In one embodiment of the present invention, a medical image of a patient is received. A current segmentation context is automatically determined based on the medical image and at least one segmentation algorithm is automatically selected from a plurality of segmentation algorithms based on the current segmentation context. A target anatomical structure is segmented in the medical image using the selected at least one segmentation algorithm.

These and other advantages of the invention will be apparent to those of ordinary skill in the art by reference to the following detailed description and the accompanying drawings.

DETAILED DESCRIPTION

The present invention relates to artificial intelligence based segmentation in medical images. Embodiments of the present invention are described herein to give a visual understanding of the medical image segmentation methods. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system or available through a network system.

Medical image segmentation refers to the detection of boundaries of structures, such as organs, vessels, different types of tissue, pathologies, medical devices, etc., in medical images of a patient. Embodiments of the present invention provide multiple artificial intelligence based medical image segmentation methods, including multiple different deep learning based medical image segmentation methods. Embodiments of the present invention also provide a method and system for autonomous artificial intelligence based medical image segmentation in which a trained intelligent artificial agent performs intelligent automated recognition of segmentation tasks and intelligent automated selection and application of segmentation algorithms.

Autonomous Artificial Intelligence Based Medical Image Segmentation

In an advantageous embodiment of the present invention, a method and system for autonomous artificial intelligence based medical image segmentation utilize a trained intelligent artificial agent to perform intelligent automated recognition of segmentation tasks and intelligent automated selection and application of segmentation algorithms. This allows the intelligent artificial agent to be applied to intelligently perform various different segmentation tasks, including segmentation of different anatomical structures and segmentation in different medical imaging modalities. The intelligent artificial agent can intelligently select one or a combination of segmentation algorithms from a plurality of segmentation algorithms to perform medical image segmentation for various anatomical objects, medical imaging modalities, and/or various imaging domains or image qualities. Accordingly, instead of a user having to select an appropriate segmentation technique to perform a particular segmentation task, the artificial intelligent agent can be used to intelligently and autonomously select and apply an optimal segmentation algorithm or combination of segmentation algorithms for any segmentation task.

Figure 1:
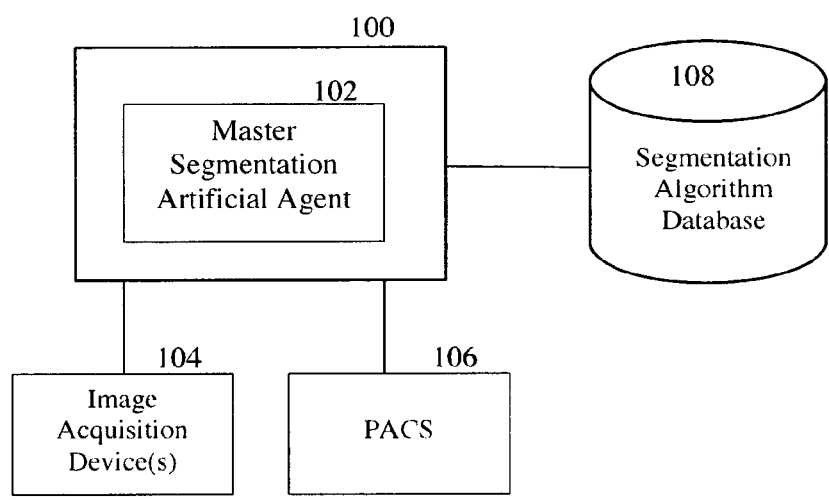
FIG. 1 illustrates a system for intelligent autonomous medical image segmentation according to an embodiment of the present invention.

FIG. 1 illustrates a system for intelligent autonomous medical image segmentation according to an embodiment of the present invention. As shown in FIG. 1, a master segmentation artificial agent 102 is run on a computer system 100. The computer system 100 communicates with one or more image acquisition device 104, a picture archiving and communication system (PACS) 106, and a segmentation algorithm database 108. The computer system 100 can be implemented using any type of computer device and includes computer processors, memory units, storage devices, computer software, and other computer components. In one embodiment, the computer system 100 can be implemented using a local computer device with respect to the image acquisition device 104 and/or the PACS 106. In a possible implementation, the computer system 100 running the master segmentation artificial agent 102 and the image acquisition device 104 can be implemented as a single device. In another possible implementation, the computer system running the master segmentation artificial agent 102 can be implemented as part of the PACS 106. In another possible implementation, the computer system 100 running the master segmentation artificial agent 102 can be implemented or as a separate local computer device (e.g., workstation) that communicates wirelessly or via a direct wired connection with the image acquisition device 104 and/or the PACS 104. In a possible embodiment, the computer system running the master segmentation artificial agent 102 can be a mobile device, such as a smart phone or tablet. In another possible embodiment, the computer system 100 running the master segmentation artificial agent 102 can be implemented on a remote cloud-based computer system using one or more networked computer devices on the cloud-based computer system. In this case, medical images of patients can be transmitted to a server of the cloud-based computer system, the master segmentation artificial agent 102 can be run as part of a cloud-based service to perform medical image registration, and the segmentation results can then be returned to a local computer device.

The image acquisition device 104 can be any type of medical image acquisition device, such as a CT scanner, MR scanner, C-arm image acquisition device, ultrasound device, etc. Medical images of a patient can be acquired using the image acquisition device 104, and the medical images can be sent to the computer system 100 running the master segmentation artificial agent 102 and/or stored in the PACS 106. Multiple image acquisition devices 104 of different medical imaging modalities may communicate with the computer system 100 running the master segmentation artificial agent 102. The PACS 106 stores medical images of various modalities for various patients in a digital format. For example, the PACS 106 can use the Digital Imaging and Communications in Medicine (DICOM) format for storage and transfer of medical images. The computer system 100 running the master segmentation artificial agent 102 can retrieve medical images stored in the PACS 106. Segmentation results extracted from the medical images can also be stored in the PACS 106.

The segmentation algorithm database 108 stores a plurality of automated artificial intelligence based segmentation algorithms. Each segmentation algorithm stored in the segmentation algorithm database 108 includes a set of computer program instructions that define a computer-based method for automatic medical image segmentation. When the master segmentation artificial agent 102 one or more of the segmentation algorithms stored in the segmentation algorithm database 108 to perform a medical image segmentation task, the corresponding computer program instructions can be loaded into a memory of the computer system 100 can run on one or more processors of the computer system 100 to perform the segmentation task. In a possible implementation, the segmentation algorithm database 108 can stored in a storage device of the computer system 100 running the master segmentation artificial agent 102. In another possible implementation, the computer system 100 running the master segmentation artificial agent 102 can access the segmentation algorithm database 108 via a local network. In another possible implementation, the segmentation algorithm database 108 can be stored in a cloud-based computer system, and the computer system 100 running the master segmentation artificial agent 102 can access the segmentation algorithm database 108 via a remote server over a data network, such as the Internet.

The segmentation algorithms stored in the segmentation algorithm database 108 can include a plurality of deep learning based medical image segmentation methods, each of which including a respective trained deep neural network architecture for performing medical image segmentation. For example, the segmentation algorithms can include the deep learning based segmentation algorithms described below, including segmentation using a deep neural network (DNN) that integrates shape priors through joint training, non-rigid shape segmentation method using deep reinforcement learning, segmentation using deep learning based partial inference modeling under domain shift, segmentation using a deep-image-to-image network and multi-scale probability maps, and active shape model based segmentation using a recurrent neural network (RNN). The segmentation algorithm database may include other deep learning based segmentation algorithms as well, such as marginal space deep learning (MSDL) and marginal space deep regression (MSDR) segmentation methods described in U.S. Pat. No. 9,668,699, entitled "Method and System for Anatomical Object Detection Using Marginal Space Deep Neural Networks," issued Jun. 6, 2017, and U.S. Patent Publication No. 2016/0174902, entitled "Method and System for Anatomical Object Detection Using Marginal Space Deep Neural Networks," filed Feb. 26, 2016, the disclosures of which are incorporated herein by reference in their entirety. It is also possible that the segmentation algorithm database 108 can also store various other non-deep learning based segmentation algorithms, including but not limited to machine-learning based segmentation methods (e.g., marginal space learning (MSL) based segmentation), graph cuts segmentation methods, region-growing based segmentation methods, and atlas-based segmentation methods.

The segmentation algorithm database 108 stores multiple versions of each segmentation algorithm corresponding to different target anatomical structures and different medical imaging modalities. For deep learning based segmentation algorithms, each version corresponding to a specific target anatomical structure and a specific medical imaging modality includes a respective trained deep network architecture with parameters (weights) learned for segmentation of that target anatomical structure in that imaging modality. For a particular anatomical structure and a particular imaging modality, the segmentation algorithm database 108 can also store multiple versions corresponding to different imaging domains and/or image quality levels. For example, for CT segmentation tasks, different versions of segmentation algorithms can include deep learning architectures trained using high-dose and low-dose CT training images. Similarly, different deep learning architectures can be trained and stored using images with different signal-to-noise ratios. Accordingly, when the master segmentation artificial agent 102 selects one or more segmentation algorithms from the those stored in the segmentation algorithm database 108, the master segmentation artificial agent 102 selects not only the type of segmentation algorithm to apply, but the specific versions of segmentation algorithms that are best for performing the current segmentation task.

The master segmentation artificial agent 102 is a trained intelligent artificial agent that automatically recognizes a current segmentation context based on medical images of a patient and automatically selects one or more of the segmentation algorithms in segmentation algorithm database 108 to perform segmentation of the medical images based on the current segmentation context. The master segmentation artificial agent 102 is an intelligent artificial agent that is implemented on one or more computers or processors of computer system 100 by executing computer program instructions (code) loaded into memory. The master segmentation artificial agent 102 observes the medical image to be segmented and autonomously acts to select a segmentation strategy using a segmentation policy learned using machine learning.

According to an advantageous embodiment, the master segmentation artificial agent 102 can select an optimal segmentation strategy for different image types, imaging domains, and image qualities. As medical imaging scanner technology advances, the medical imaging data that is produced by the scanner changes over a period of time. This change is typically manifested in technical parameters such as image resolution, noise characteristics, etc. For example, with the advent of low-dose CT imaging, the signal-to-noise-ratio of the images was considerably different than the signal-to-noise-ratio in images generated by non-low-dose CT scanners. Another example is the images produced by MR scanners with compressed sensing based reconstruction. A pre-trained segmentation algorithm that has not been trained on a large database of such new images may not have the ability to generalize on these new images. The master segmentation artificial agent 102 can automatically manage and orchestrate a set of segmentation algorithms to achieve a desired segmentation task. For example, the master segmentation artificial agent 102 may first analyze the medical image to be segmented, and based on the analysis of the medical image, determine versions of one or more of the segmentation algorithms with parameter settings that will achieve the best segmentation results for the target segmentation task. The master segmentation artificial agent 102 may select a single segmentation algorithm (version) to perform the segmentation or may select multiple segmentation algorithms and then fuse the segmentation results from the selected segmentation algorithms and output a unified segment result.

The master segmentation artificial agent 102 can also perform online adaptation of the segmentation algorithms. For example, the master segmentation artificial agent 102 can control one or more of the segmentation algorithms in the segmentation algorithm database 108 to be re-trained based on new training data. In a possible embodiment, one or more of the segmentation algorithms stored in the segmentation algorithm database 108 can be deep learning segmentation algorithms with respective trained deep neural networks that were acquired pre-trained or trained using publically available data, and the master segmentation artificial agent 102 can control those segmentation algorithms to be re-trained using image data of domain specific to a clinical site at which the master segmentation artificial agent 102 is running or using image data that is private to the clinical site. In this way the master segmentation artificial agent 102 can more specifically tailor the trained deep learning segmentation algorithms available in the segmentation algorithm database 108 to the specific segmentation tasks performed at the clinical location without transmitting private patient data to an outside party for training.

The master segmentation artificial agent 102 can be trained based on training data including medical images and known ground truth segmentation results for given segmentation tasks. Segmentation can be performed on each of the training samples using each of the segmentation algorithms stored in the segmentation algorithm database 108 and the resulting segmentation results can be compared to the ground truth segmentation results to calculate confidence measures for each of segmentation algorithms. Synthetic training samples can also be generated from the real medical image training samples by converting the real medical image training samples to synthetic images having different imaging characteristics (e.g., noise levels, resolution, etc.). For example, synthetic high-dose and/or low-dose CT images can be generated from normal dose CT images or synthetic images with randomly added image noise can be generated. The synthetic images with the different characteristics are also segmented using each of the segmentation algorithms and confidence levels for the segmentation algorithms are calculated based on the synthetic samples. A machine learning based mapping is then trained based on the training data (real and synthetic) to select a best segmentation algorithm or combination or segmentation algorithms based on image characteristics of the input images. For example, a deep neural network (DNN) can be trained to deep learning techniques, such as deep reinforcement learning, to select one or more segmentation algorithms for a given segmentation task based on characteristics of the medical image to be segmented. At runtime, when a medical image to be segmented is received, the master segmentation artificial agent 102 uses the trained machine learning based mapping to select the best segmentation algorithm or combination of segmentation algorithms to perform the segmentation task based on the image characteristics of the received medical image. In an exemplary implementation in which the master segmentation artificial agent 102 uses a trained DNN to select the one or more segmentation algorithms, the medical image data can be directly input to the trained DNN, which can automatically extract characteristics or features used to determine which segmentation algorithm or algorithms to select.

In another advantageous embodiment, the master segmentation artificial agent 102 can be applied to select an optimal segmentation strategy across multiple different target anatomies and imaging modalities. Typically, medical image segmentation algorithms are designed and optimized with a specific context of use. For example, algorithms designed for segmenting tubular structures generally perform well in arteries and veins, while algorithms designed for "blob" like structures are well suited for organs such as the heart, brain, liver, etc. The master segmentation artificial agent 102 can automatically identify the context of use (e.g., the target anatomical structure to be segmented) and automatically switch between different segmentation algorithms for different target anatomical structures.

A machine learning based classifier (e.g., probabilistic boosting tree (PBT), random forests classifier, deep neural network (DNN), etc.) can be trained to recognize an anatomical entity in a view of a medical image. In a possible implementation, as a user visualizes a medical image on a screen, the trained classifier can be applied to automatically detect what anatomical structure or structures are currently being visualized on the screen. The master segmentation artificial agent 102 can then select one or more segmentation algorithms for segmenting the anatomical structure or structures currently being visualized on the screen. For example, if the user is currently visualizing a portion of a medical image including the heart on the screen, a heart-specific segmentation algorithm can be automatically initiated by the master segmentation artificial agent 102. If the user then clicks in the aorta, a vascular segmentation may then be automatically initiated by the master segmentation artificial agent 102. In this way, the user is not required to pick and choose different segmentation algorithms for achieving different segmentation tasks. When multiple segmentation algorithms in the segmentation algorithm database 108 can be used to segment a particular anatomical structure, the master segmentation artificial agent 102 can utilize a machine learning based mapping (e.g., DNN), trained as described above, to select the best segmentation algorithm for the segmentation task based on the medical imaging modality and/or other image characteristics of the medical image to be segmented.

Although the master segmentation artificial agent 102 acts autonomously to select one or more segmentation algorithms, in a possible implementation, a user (or a clinical site) may be provided with a manual override option (for example on a user interface displayed on a display device) that allows the user to override the master segmentation artificial agent 102 and manually chose a specific segmentation algorithm. Rules controlling the use of the manually override can be defined and/or adjusted by a user.

Figure 2:
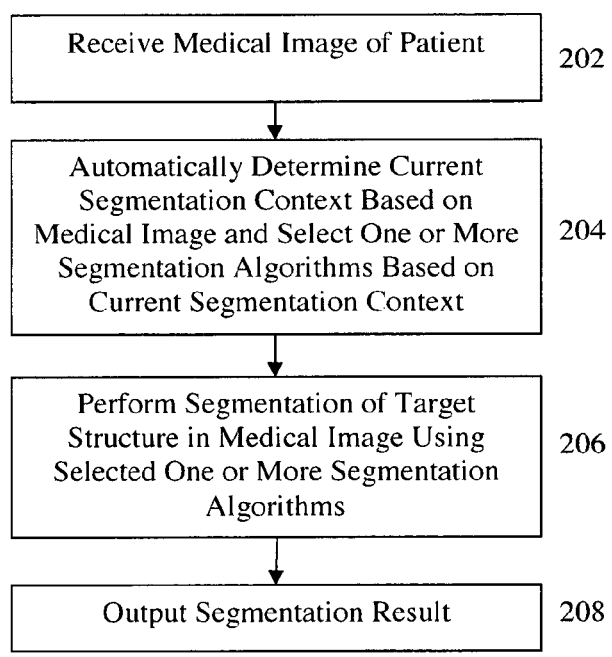
FIG. 2 illustrates a method for intelligent autonomous medical image segmentation according to an embodiment of the present invention.

FIG. 2 illustrates a method for intelligent autonomous medical image segmentation according to an embodiment of the present invention. Referring to FIG. 2, at step 202, a medical image of a patient is received. The medical image can be a 2D image, 3D image, or 4D (3D+time) image. The medical image can be acquired using any medical imaging modality, such as computed tomography (CT), magnetic resonance imaging (MRI), ultrasound, x-ray, DynaCT, positron emission tomography (PET), etc. The medical image may be received directly from an image acquisition device 104, such as a CT scanner, MRI scanner, ultrasound device, C-arm image acquisition device, etc., or may be received by loading a previously stored medical image from a memory or storage of a computer system (e.g., PACS 106) or receiving the medical images in an electronic transmission from another computer system.

At step 204, a current segmentation context is automatically determined based on the medical image and one or more segmentation algorithms are automatically selected based on the current segmentation context. The current segmentation context that is automatically determined can include any or all of one or more target anatomical structures to be segmented, a current imaging modality, and/or other image characteristics (e.g., noise level, resolution, etc.) of the received medical image. In an advantageous embodiment, the master segmentation artificial agent 102 can utilize a machine learning based classifier to automatically identify one or more anatomical structure in the received medical image. The master segmentation artificial agent 102 can then automatically select a segmentation algorithm or a combination of segmentation algorithms from the segmentation algorithm database 108 to perform the segmentation of the identified one or more target anatomical structure. The master segmentation artificial agent 102 may utilize a trained machine learning based mapping (e.g., DNN) to select between multiple segmentation algorithms that can perform segmentation of the identified one or more target anatomical structure. The machine learning based mapping may also consider imaging modality and/or other imaging characteristics. In another advantageous embodiment, the master segmentation artificial agent 102 can utilize a trained machine learning based mapping (e.g., DNN) to select a segmentation algorithm or combination of segmentation algorithms in the segmentation algorithm database 108 that have optimal parameter settings for performing the segmentation in the received medical image based on image characteristics (e.g., noise resolution, etc.) of the received medical image. Multiple versions of various segmentation algorithms corresponding to various target anatomical structures, imaging modalities, imaging domains/image qualities, etc. can be stored in the segmentation algorithm database 108. Each version of a segmentation algorithm can be interpreted to be a separate segmentation algorithm and when the master segmentation artificial agent 102 "selects a segmentation algorithm," it is to be understood that the master segmentation artificial agent 102 selects a particular version of the segmentation algorithm.

At step 206, a target anatomical structure in the medical image is segmented using the selected one or more segmentation algorithms. In particular, the computer program instructions corresponding to the selected one or more segmentation algorithms are loaded into a memory of a computer system and executed by one or more processors of a computer system to perform the segmentation of the target anatomical structure in the medical image. Additional details regarding various artificial intelligence based segmentation algorithms are described below.

At step 208, the segmentation result is output. The segmentation result can be output by displaying the segmentation result on a display device of a computer system. In the case in which a single segmentation algorithm was selected in step 204 and used to perform the segmentation in step 206, the segmentation result from the selected segmentation algorithm is output. In the case in which multiple segmentation algorithms were selected in step 204 and used to perform the segmentation in step 206, the multiple segmentations results from the multiple segmentation algorithms are fused into a single segmentation result, which is output. For example, the multiple segmentation results can be fused by averaging the segmentation results using an unweighted average or by weighting the segmentation results from the different segmentation algorithms according to a segmentation strategy automatically selected (e.g., using a trained DNN) in step 204.

In a possible embodiment, it can be determined, either automatically or based on user input, whether the segmentation result is acceptable or whether additional processing is needed. If it is determined that additional processing is needed, the method can return to step 204 at which one or more additional segmentation algorithms can be selected, and the segmentation results from the one or more additional segmentation algorithms can be combined with or replace the previous segmentation result.

Various artificial intelligence based medical image segmentation methods are described below. These methods, along with other existing segmentation methods, can be stored in the segmentation algorithm database 108 and used in the method of FIG. 2. Each of the segmentation methods described herein may also be used as a stand-alone medical image segmentation method as well.

Organ/Anatomical Object Segmentation by Integrating Priors into Deep Neural Networks Through Joint Training Automatic organ segmentation is fundamental in medical image analysis, but remains a challenging task despite numerous efforts in developing segmentation methods. Machine learning based methods have been shown to be powerful tools and have had success in medical image segmentation. Given limited data with annotations, integrating priors and domain knowledge is important to improve segmentation accuracy and robustness. One such prior is shape. Explicit modeling of shape priors as a separate module in the segmentation pipeline, such as using an active shape model, has demonstrated significant positive impact to regularize segmentation. Recent trends in deep learning show that an end-to-end learning system is feasible and advantageous to allow the segmentation to be truly data-driven. However, how to integrate priors, such as shape priors, into deep neural networks (DNN) has remained unsolved and challenging. This embodiment of the present invention provides a method for integrating priors into deep neural networks for organ (or other anatomical object) segmentation in medical images.

In this embodiment of the present invention, a joint learning framework is used to integrate priors to boost the modeling power of deep neural networks for organ segmentation. In an advantageous implementation, distance maps derived from segmentation masks can be used as implicit shape priors, and segmentation DNNs can be learned/trained in conjunction with the distance maps. In addition, the main target segmentation DNN, DNNs from other priors can be introduced for regularization to help improve model performance. Such learning frameworks are not limited to integration of distance maps, but can be similarly applied to integrate other priors as well. This embodiment provides improved accuracy of the final segmentation result as compared to conventional computer-based segmentation methods because additional information is integrated into the deep learning architecture that performs the segmentation.

Figure 3:
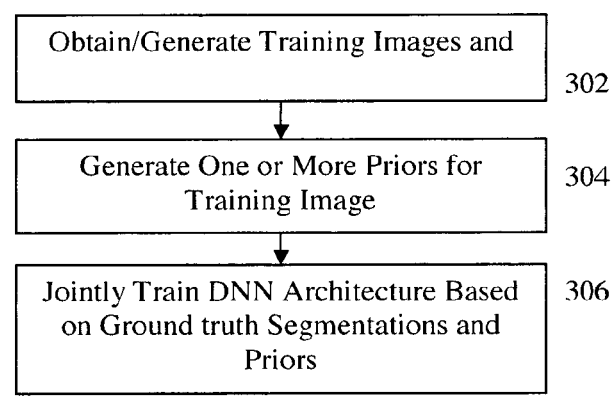
FIG. 3 illustrates a method for training a deep learning architecture for anatomical object segmentation using a joint learning framework to integrate priors according to an embodiment of the present invention.

FIG. 3 illustrates a method for training a deep learning architecture for anatomical object segmentation using a joint learning framework to integrate priors according to an embodiment of the present invention. Referring to FIG. 3, at step 302 training images and corresponding ground truth segmentations (segmentation masks) are obtained or generated. Medical images with already existing ground truth segmentations may be obtained by loading the medical images and ground truth segmentations from a database. Medical images without ground truth segmentations can be manually annotated to generate ground truth segmentations.

At step 304, one or more priors are generated for each of the training images. According to an advantageous embodiment, distance maps are generated for each of the training images and used as implicit shape priors. The distance map for each training image is generated using the corresponding ground truth segmentation mask. In particular, for a given training image, a distance map is generated by assigning an intensity value for each pixel/voxel corresponding to a distance from that pixel/voxel to a nearest point on the target anatomical structure. Other priors may be generated as well for each training image. For example, from the annotated mask/contour, gradient maps can be generated to provide priors for edge orientations. In general, any derivatives/feature-maps that are calculated from the training data can be used as priors in this invention. Such derived priors may act regularizers to help optimize the neural network training and online performance.

Figure 4:
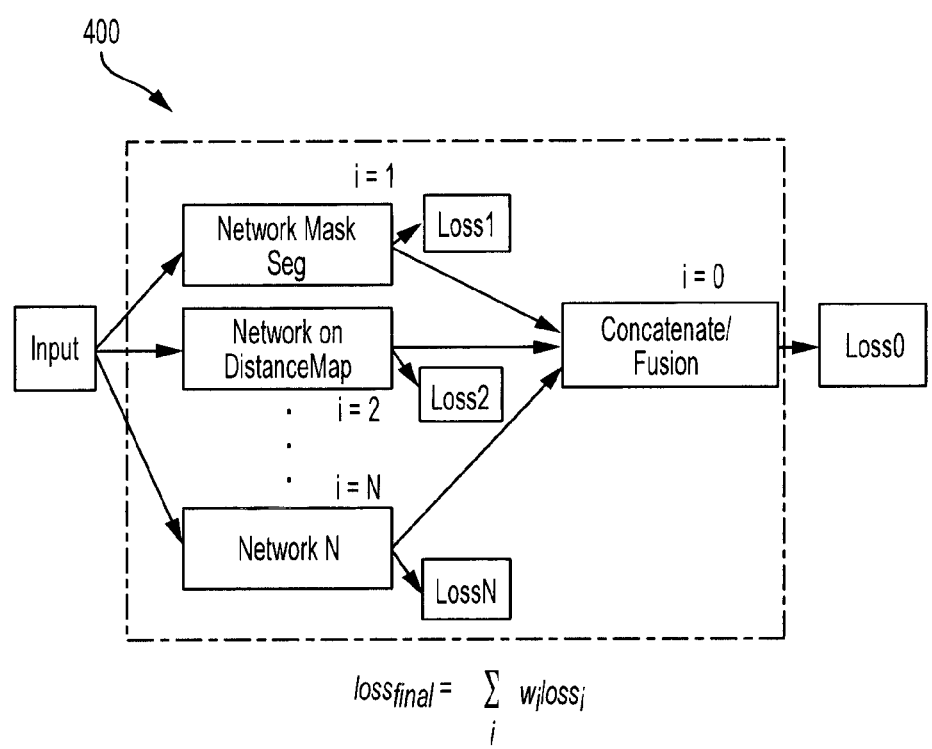
FIG. 4 illustrates a joint training framework for training a DNN architecture according to an embodiment of the present invention.

At step 306, a deep neural network (DNN) architecture is jointly trained based on the ground truth segmentations (segmentation masks) and the priors generated for the training images. FIG. 4 illustrates a joint training framework for training a DNN architecture according to an embodiment of the present invention. As shown in FIG. 4, a DNN architecture 400 includes multiple component networks (i=1, 2, . . . N) and a fusion network (i=0), and the weights $w_i$ of the component networks and the fusion network are learned using joint training to minimize a final loss function that is a combination of the individual loss functions of all the networks: $loss_{final} = \Sigma_i w_i loss_i$. Through error back-propagation during joint training, these component networks will influence and regularize each other.

The component networks i=1, 2, . . . , N are deep neural networks trained to estimate the segmentation mask (i=1) and one or more priors (i=2, . . . , N) from an input medical image. As shown in FIG. 4, Network 1 is a deep neural network trained on the segmentation masks and Network 2 is a deep neural network trained on the distance maps. Network 1 inputs a medical image and estimates a segmentation mask, and the loss function for Network 1 (Loss1) is an error between the estimated segmentation masks and the ground truth segmentation masks over the set of training samples. Network 2 inputs a medical image and estimates a distance map, and the loss function for Network 2 (Loss2) is an error between the estimated distance maps and the ground truth distance maps (generated in step 304) over the set of training samples. Other priors may be used as well to train additional component networks, although it is also possible that no additional priors other than the segmentation mask and distance map are used. The fusion network (i=0) inputs the segmentation mask and priors estimated by component networks (i=1, 2, . . . , N) and learns weights to combine the various outputs of the component networks to minimize a loss function (Loss0) that is an error between the final segmentation results output by the fusion network and the ground truth segmentation results over the set of training samples. The combination weights in the fusion network are not predefined, but learned from the training data.

The entire DNN architecture 400 is an end-to-end (i.e., from input raw image data to output labels for the pixels/voxels of the medical image providing the segmentation result) deep neural network. The training procedure is performed end-to-end as well using well-known back-propagation optimization methods to learn weights $w_i$ that minimize the final loss function $loss_{final}$. In an advantageous embodiment, each component network, i.e., Network i is a deep neural network. In an exemplary implementation, each component network, i.e., Network i, can be a fully convolutional network (FCN), but the present invention is not limited thereto and other deep network architectures may be used as well. In this exemplary implementation, the entire medical image can be input to each component network. The fusion/concatenation network (i=0) may be implemented as a single layer or a deep neural network. In a possible implementation, the component networks can be pre-trained individually, then fed for joint training. The deep neural networks for different priors may be heterogeneous in their architectures according to different varieties of priors. One advantage of the framework illustrated in FIG. 4 is that it is modular and can be easily expanded. That is, an additional prior can be easily integrated by adding an additional component network. The framework is also flexible, as the focus on the various losses can be adjusted to adapt the DNN architecture to different segmentation tasks. Once the DNN architecture with integrated priors is trained, the trained DNN architecture can be stored in a memory or storage device of a computer system and used to perform online segmentation of newly received medical images.

Figure 5:
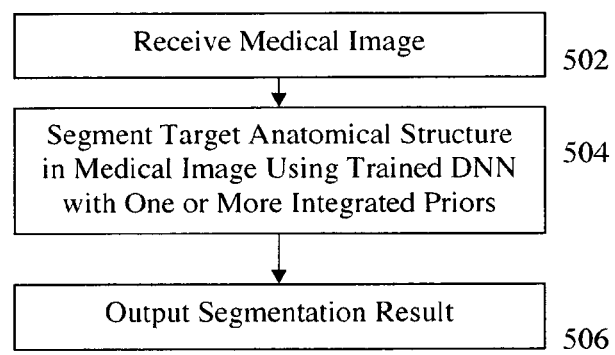
FIG. 5 illustrates a method of segmenting a target anatomical structure using a deep neural network with integrated priors according to an embodiment of the present invention.

FIG. 5 illustrates a method of segmenting a target anatomical structure using a deep neural network with integrated priors according to an embodiment of the present invention. For example, the method of FIG. 5 can be used for organ segmentation. Referring to FIG. 5, at step 502, a medical image of the patient is received. The medical image can be a 2D image, 3D image, or 4D (3D+time) image. The medical image can be acquired using any medical imaging modality, such as computed tomography (CT), magnetic resonance imaging (MRI), ultrasound, x-ray, DynaCT, positron emission tomography (PET), etc. The medical image may be received directly from an image acquisition device, such as a CT scanner, MRI scanner, ultrasound device, C-arm image acquisition device, etc., or may be received by loading a previously stored medical image from a memory or storage of a computer system or receiving the medical images in an electronic transmission from another computer system.

At step 504, the target anatomical structure (e.g., organ) is segmented in the medical image using a trained DNN with one or more integrated priors. The trained DNN with the integrated priors is trained as described above in FIGS. 3 and 4. The trained DNN includes component networks, including a component network trained based on segmentation masks, one or more component networks trained based on priors, and a fusion network. In an exemplary implementation, the trained DNN includes a first component network trained based on segmentation masks and a second component network trained based on distance maps. The raw image data of the medical image is input to the trained DNN and individual segmentation results are calculated using the component networks (i=1, 2, . . . , N). The individual segmentation results are then input to the fusion network (i=0) and the fusion network fuses the individual segmentation results to generate a final segmentation result.

At step 506, the segmentation result is output. In particular, the final segmentation result generated from the fusion network of the trained DNN is output. The segmentation result can be output by displaying the segmentation result on a display device of a computer system.

Figure 6:
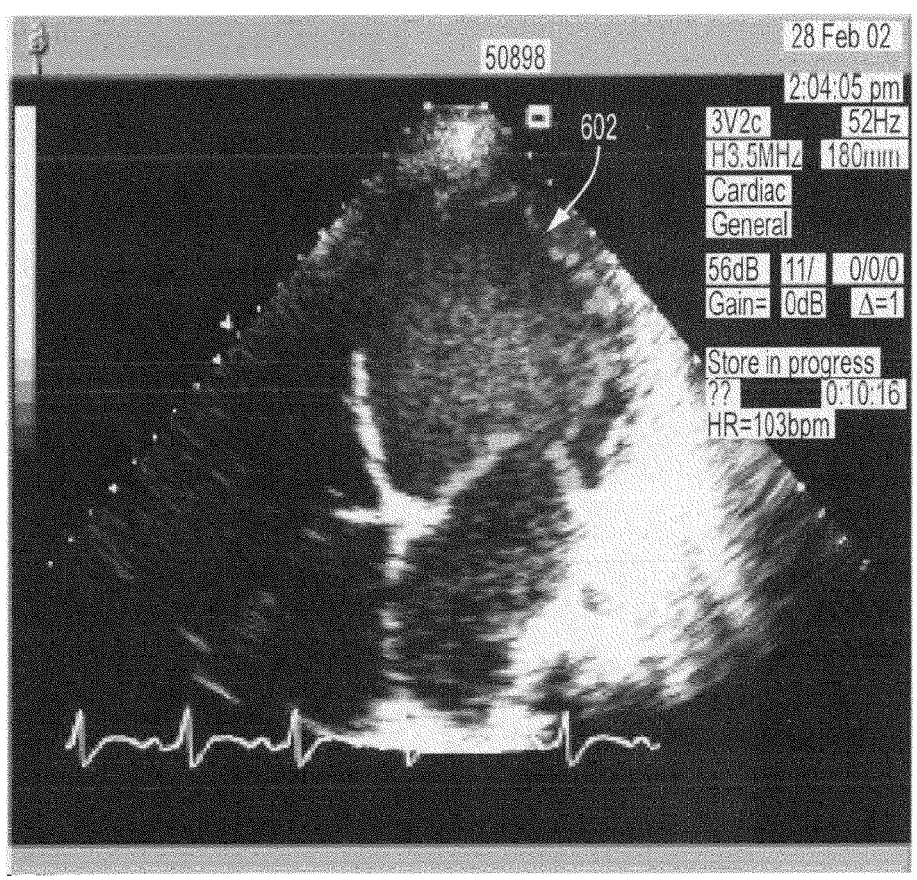
FIG. 6 illustrates an exemplary segmentation result for left ventricle segmentation in 3D echocardiography using the method of FIG. 5.

FIG. 6 illustrates an exemplary segmentation result for left ventricle segmentation in 3D echocardiography using the method of FIG. 5. As shown in FIG. 6, a segmentation mask 602 showing the segmented left ventricle is overlaid on the original 2D echocardiography image. For the left ventricle segmentation, 14075 images were randomly selected for training the DNN architectures and 1453 remaining images were used for benchmarking. Two component networks were included: the main target network to learn the segmentation mask was implemented using a VGG-FCN8s with two-level output, i.e., target and background; and the component network for the distance map was implemented using a VGG-FCN8s, but with 64-level output. Standard Dice coefficient was used for accuracy evaluation. Table 1 shows the accuracy of joint estimation using the mask and the distance map as compared to the accuracy of using the mask only. The efficacy of the above describe segmentation method can be observed in Table 1, as the accuracy increases with the joint estimation as compared to mask only.

TABLE 1

| Dice coefficient | Mean | Std | Median |
| --- | --- | --- | --- |
| Mask only | 0.7220 | 0.1468 | 0.7612 |
| Joint (mask + distmap) | 0.7997 | 0.0934 | 0.8160 |

Deep Reinforcement Learning for Non-rigid Shape Segmentation in Medical Images

Automatically segmenting a target object in a medical image is often a prerequisite for disease quantification and diagnosis. Marginal space learning (MSL) is an efficient machine-learning based method for object detection/segmentation in medical images. MSL has been applied for segmenting various organs (e.g., cardiac chambers, liver, kidney, lung, etc.) in various medical imaging modalities (e.g., CT, MR, ultrasound, X-ray, etc.). However, the segmentation accuracy of MSL needs further improvement for some non-rigid objects with a large shape variation, such as the liver. Compared to other organs, the liver is especially difficult to segment. The liver is the largest organ in the human body and it is highly deformable. Due to forces from neighboring organs, such as the heart, kidneys, and stomach, the shape of the liver changes by a large amount.

In MSL, non-rigid shape segmentation is split into two stages: pose estimation and boundary delineation. Pose estimation is formulated as a parameter estimation problem (i.e., estimating the nine pose parameters for a 3D object: three translation parameters, three rotation parameters, and three scaling parameters). An active shape model (ASM) is used for boundary delineation, where an iterative local search is applied for each surface mesh point. The ASM has no explicit objective functions to optimize and the whole system is not trained end-to-end.

In this embodiment, the non-rigid shape segmentation task (e.g., liver segmentation in CT or MRI images) is formulated as a parameter estimation problem. A non-rigid shape is represented as a set of parameters. According to an advantageous embodiment, deep reinforcement learning (DRL) is used to train a deep neural network (DNN) to estimate the shape parameters of a non-rigid object (e.g., the liver) in a medical image.

There are many ways to represent a non-rigid shape. In an advantageous implementation, a statistical shape model is used since it can capture the major deformation modes with a few parameters. In an offline training phase, a statistical shape model of the target anatomical object is generated based on annotated training data. To build a statistical shape model, N shapes are used and each is represented by M points with correspondence in anatomy. Stacking the 3D coordinates of these M points results in a 3M dimensional vector $X_i$, i=1, 2, ..., N, to represent a shape i. To remove the relative translation, orientation, and scaling, all shapes can first be jointly aligned using generalized Procrustes analysis to get the aligned shapes $x_i$, i=1, 2, ..., N. The mean shape x is calculated as the simple average of the aligned shapes. The shape space spanned by these N aligned shapes can be represented as a linear space with K=min{3M−1, N−1} eigen vectors, $V_1, \ldots, V_K$, based on principal component analysis (PCA).

A new shape y in the aligned shape space can be represented as:

$$y = \bar{x} + \Sigma_{i=1}^{K} c_i V_i + e, \quad (1)$$

where $c_i$ is the PCA coefficient and e is a 3M dimensional vector for the residual error. Using the statistical shape model, a non-rigid shape can be represented parametrically as (T, R, S, $c_1, \ldots, c_K$, $\bar{x}$, e), where T,R,S represent the translation, rotation, and scaling, respectively, to transfer a non-rigid shape in the aligned space back to the world coordinate system. With this representation, the non-rigid shape segmentation (or boundary delineation) can be converted to a parameter estimation problem. Among all of these parameters, x is fixed and e is sufficiently small if K is large enough (i.e., with enough training shapes). Therefore, we only need to estimate (T, R, S, $c_1, \ldots, c_K$). It can be noted that MSL only estimates the rigid part (T,R,S) of the transformation.

According to an advantageous embodiment, DRL is used to train a DNN to search for both the rigid and non-rigid shape parameters $P_s=(T, R, S, c_1, \ldots, c_K)$. DRL does not perform an exhaustive search of the parameter space (i.e., testing all possible combinations of shape parameters). Given an initial guess of the parameters, DRL follows a specific path (determined by the learned policy) to the optimal solution, so it is very efficient. DRL is an incremental search approach, which is different from a regression based approach. A regression based approach potentially can directly output the final shape parameter starting from an initial guess. Instead, DRL performs incremental update of the shape parameters. At each iteration, one shape parameter is updated by a small fixed amount (increase or decrease the parameter value). For example, for an object position search, a current guess can be shifted by one pixel (+1 or −1) in one direction (i.e., x, y, or z for a 3D object). Therefore, DRL can tolerate occasional errors during the searching process.

DRL is used to learn a policy for estimating the parameters representing a non-rigid shape based on a set of training samples. The learned policy assigns rewards to actions corresponding to adjusting the various parameters based on the observed states of the input training samples. A DNN, such as a convolutional neural network (CNN), is trained to estimate action-values for the various actions that best match the rewards over the set of training samples. Accordingly, for a current state of a set of parameters representing a non-rigid shape in a medical image, the trained DNN predicts action-values corresponding to adjustments to each of the parameters based on the learned policy. The parameter adjustment with the highest predicted action value is performed and the process is iterated to incrementally adjust the parameters to find a final set of parameters that best represents the non-rigid shape in the medical image.

Figure 7:
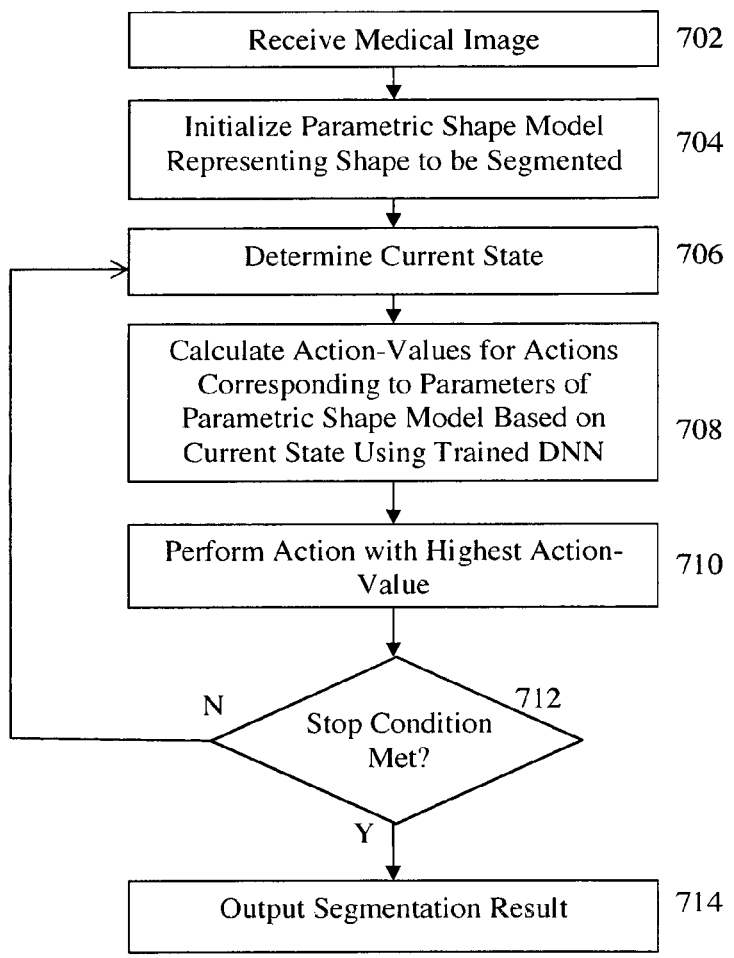
FIG. 7 illustrates a method for deep reinforcement learning (DRL) based segmentation of a non-rigid anatomical object in a medical image according to an embodiment of the present invention.

FIG. 7 illustrates a method for DRL based segmentation of a non-rigid anatomical object in a medical image according to an embodiment of the present invention. In an exemplary embodiment, the method of FIG. 7 can be used for liver segmentation in a medical image. Referring to FIG. 7, at step 702, a medical image of the patient is received. The medical image can be a 2D image, 3D image, or 4D (3D+time) image. The medical image can be acquired using any medical imaging modality, such as computed tomography (CT), magnetic resonance imaging (MRI), ultrasound, X-ray, DynaCT, positron emission tomography (PET), etc. The medical image may be received directly from an image acquisition device, such as a CT scanner, MRI scanner, ultrasound device, C-arm image acquisition device, etc., or may be received by loading a previously stored medical image from a memory or storage of a computer system or receiving the medical images in an electronic transmission from another computer system.

At step 704, a parametric shape model representing the shape of the anatomical object to be segmented is initialized.

As described above, a statistical shape model is used to represent the non-rigid shape and the parameters to be estimated are (T, R, S, $c_1, \ldots, c_K$). In a possible implementation, the parameters can be initialized so that the initial estimate of the shape corresponds to the mean shape $\bar{x}$ of the learned statistical shape model positioned at the center of the medical image (with no rotation or scaling). In another possible embodiment, a user input can be received corresponding to an approximate position of the non-rigid anatomical object and the parameters can be initialized with the mean shape $\bar{x}$ positioned at the user input location. In another possible embodiment, the shape parameters can be randomly initialized.

At step 706, the current state of the estimated non-rigid shape is determined. The current state to be input to the trained DNN can be represented in various ways. In DRL, the trained DNN may be trained by training a convolutional neural network to extract an image feature vector with a predefined dimension, which is fed to another neural network to learn the policy. In one embodiment, the original medical image and the current estimate of the shape parameters can be used to represent the current state. In this case, image features can be extracted from the input original medical image and fed together with the current shape parameter to estimate the policy learning network. Along the searching trajectory, the image features are fixed but the current shape parameters keep updating.

In another embodiment, the current rigid shape parameters can be embedded to the medical image. For example, in DRL based landmark detection an image patch is cropped centered at the current estimate of the landmark position. Once the current position estimate is updated, a new image patch is cropped. This technique can be extended to search for the orientation (rotation) and size (scaling) of an object. Instead of cropping a fixed-sized image patch aligned with the imaging grid, an oriented image patch can be cropped using the current size estimate. Accordingly, such an image patch incorporates the current (T, R, S) parameters. In this case, the current non-rigid parameters ($c_1, \ldots, c_K$) are input to the trained DNN together with the rigidly aligned image patch to represent the current state.

In another embodiment, the non-rigid shape parameters ($c_1, \ldots c_K$) can be embedded to the image patch as well. The current shape parameters $P_s$ can be converted to a non-rigid shape by plugging $P_s$ into Equation (1). If the current estimate of $P_s$ is close to the ground truth, the corresponding non-rigid shape should delineate the object boundary well. Next, a deformation field can be estimated for warping the current shape to the mean shape $\bar{x}$, e.g., using a thin plate spline (TPS). The estimated TPS can be applied to the cropped image patch. After warping, such a non-rigidly aligned image patch embeds both the rigid and non-rigid shape parameters. Therefore, it is sufficient to feed only this image patch to the policy network. If the current shape estimate is correct, the non-rigid object in the aligned image patch takes the shape of $\bar{x}$. The policy network can determine an optimal action (i.e., update of a shape parameter) based on the difference between the mean shape and the shape in the non-rigidly aligned image patch.

At step 708, action-values are calculated for parameters of the parametric shape model based on the current state using the trained DNN. The current state is input to the trained DNN (policy network), and the trained DNN calculates action-values for a set of actions corresponding to adjusting each of the current shape parameters (T, R, S, $c_1, \ldots, c_K$) by increasing or decreasing by a predetermined amount. At step 710, the action with the highest action value is performed. Accordingly, one of the shape parameters is increased or decreased by a predetermined amount.

At step 712, it is determined if a stop condition has been met. For example, the stop condition can be met when it is determined that the shape parameters have converged, a loop is detected in the incremental updates of the shape parameters, or when a predetermined maximum number of iterations have been performed. If the stop condition has not been met, the method returns to step 706 and repeats steps 706-712. Accordingly steps 706-712 are repeated until the stop condition is met. When the stop condition is met, the method proceeds to step 714.

At step 714, the segmentation result is output. The final shape parameters $P_s$ are converted to the shape of the segmented non-rigid anatomical object using Equation (1). The segmented non-rigid anatomical object can be output by displaying the segmentation result on a display device of a computer system.

Figure 8:
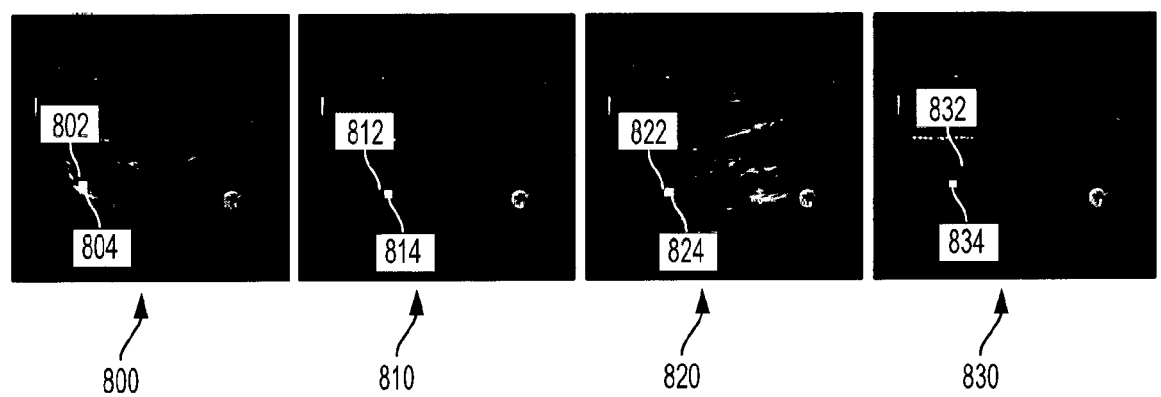
FIG. 8 illustrates exemplary anatomic landmark detection results in ultrasound images using a conventional automated landmark detection algorithm.

Landmark Detection and Segmentation Using Deep Image-to-Image Network and Multi-Scale Probability Maps Localizing clinically relevant landmarks in important in many medical activities. The time and cost makes manual landmark annotation unrealistic on retrospective large-scale studies, while inter-subject disagreement also affects real-time case-by-case studies negatively. Accordingly, a reliable automatic landmark detection algorithm is very desirable. However, reliable automatic landmark detection is challenging due to the complexity and variations of medical images, and it is difficult to provide both precise and robust automated landmark detection. FIG. 8 illustrates exemplary anatomic landmark detection results in ultrasound images using a conventional automated landmark detection algorithm. As shown in FIG. 8, ground truth landmarks 802, 812, 822, and 832 and automatically detected landmarks 804, 814, 824, and 834 are shown in ultrasound images 800, 810, 820, and 830 respectively. As can be observed in image 810 of FIG. 8, the automated landmark detection algorithm may fail to locate the exact position of the target landmark. As can be observed in image 830 of FIG. 8, the automated landmark detection algorithm may also generate outliers in some cases.

The landmark detection problem has been studied using machine learning algorithms. The commonly used approaches provide reasonable results, but they cannot guarantee both precision and robustness. Landmark detection can be considered as a binary classification problem, one class for landmark locations (positives), and the other for non-landmark locations (negatives). The positives and negatives are highly unbalanced under this configuration a trained classifier can be substantially biased, resulting in landmark detection performances that are not robust. As an alternative, landmark detection can be approached in a regression manner, where the pixel-wise relative distances to the landmark are trained to derive the estimation of the landmark location. This provides more robust results than the classification approach as multiple pixels vote for the final estimation; however, it suffers from high complexity and variation of the image context, and fails to learn precise relative distances. Recently, there have been some efforts to detect the landmark locations in a greedy manner from a random initial spot via learning an optimized action step from any location to the target. However, the learning process can only cover a subset of the almost infinite paths across the image context, and this technique can lead to major failure if not trained with adequate dataset variations. This embodiment of the present invention provides a method for automated landmark detection that improves accuracy and robustness as compared to convention landmark detection algorithms. This embodiment can also be applied perform automated segmentation of an anatomical object with similar benefits in improved accuracy and robustness.

Figure 9:
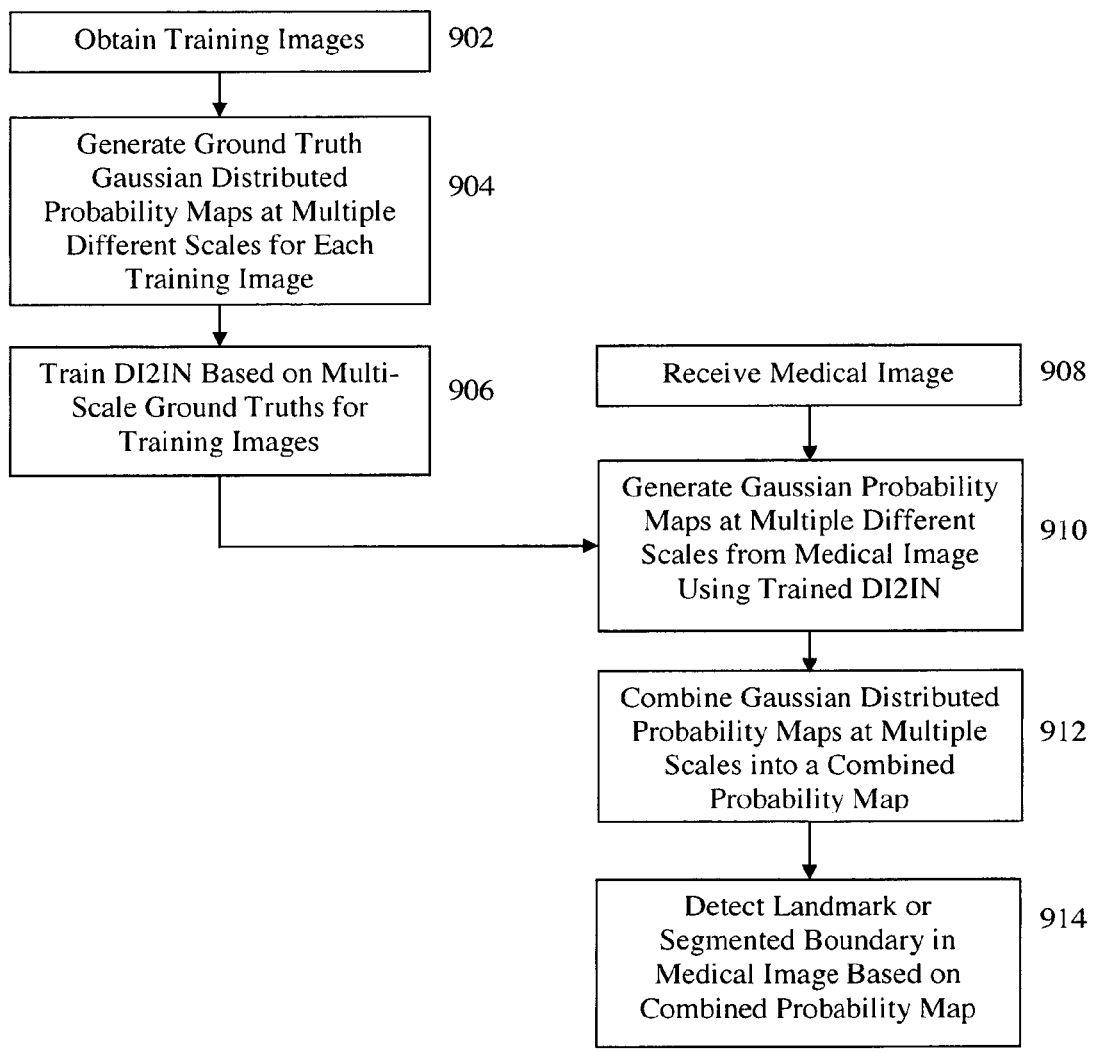
FIG. 9 illustrates a method for landmark detection or anatomical object segmentation in a medical image using a deep image-to-image network (DI2IN) and multi-scale probability maps according to an embodiment of the present invention.

FIG. 9 illustrates a method for landmark detection or anatomical object segmentation in a medical image using a deep image-to-image network (DI2IN) and multi-scale probability maps according to an embodiment of the present invention. The method FIG. 9 is described herein as detecting a landmark in a medical image, but can be similarly applied for segmenting an anatomical object by extracting a boundary of the anatomical object. Areas in which the method is adjusted to perform segmentation instead of landmark detection are explained in the following description of FIG. 9. Steps 902-906 of FIG. 9 are a training phase that are performed offline to train the DI2IN used for landmark detection or anatomical object segmentation prior to actual landmark detection or segmentation is performed on a newly received medical image.

At step 902, training images are obtained. For landmark detection, the training images are medical images with known annotated ground truth landmark locations. For anatomical object segmentation, the training images are medical image with known annotated boundaries of the target anatomical object. The training images may be obtained by loading existing annotated training images from a database. Alternatively, medical images without known ground truth annotations can be loaded from a database or acquired from a medical image acquisition device and manually annotated to generate training images.

At step 904, ground truth Gaussian distributed probability maps are generated at multiple scales for each training image. A DI2IN is a deep learning framework that maps and input medical image to an output image that provides the result of a particular image analysis task. According to an advantageous embodiment of the present invention, the ground truth output image for a target landmark in a training image is constructed using a Gaussian distributed probability map across the underlying image. The value of each pixel in the probability map is determined by the Euclidean distance to the target landmark following a given Gaussian distribution. That is, a ground truth probability map generated for a training image can be defined as:

$$J(x)=g(|x-x_l|; \sigma), \quad (2)$$

where g(t) is a Gaussian function with standard deviation σ, and $|x-x_l|$ measures the Euclidean distance from the pixel x to location $x_l$ of the target landmark. This essentially forms a Gaussian-like circle (for 2D images) or ball (for 3D images) surrounding the target landmark, and results in a ground truth probability map in which the highest value across the probability map would be at the landmark point, while almost-zero values would be observed at pixels far away from the target. By constructing the ground truth output image for landmark detection this way, the landmark detection is treated as a regression problem while focusing around the target region.

The standard deviation σ of the Gaussian distribution controls the span and steepness of the Gaussian distribution. When σ is larger, the region of interest surrounding the target landmark in the probability map will be larger, the classifier will have a larger receptive field, and thus be more robust. When a is smaller, the region of interest surrounding to target landmark will be smaller, the classifier will focus on local identification, and thus be more precise. Thus, according to an advantageous embodiment of the present invention, the ground truth for each training image is augmented to have multiple probability maps using different scales (i.e., different a values). That is, for each training image multiple probability maps are generated using different a values. The use of the different a values provides ground truth probability maps with different scales for the same underlying training image.

For anatomical object segmentation, each ground truth output image can be a Gaussian distributed probability map having a Gaussian-like band surrounding the boundary of the target anatomical object. Such a ground truth probability map generated for a training image can be defined as:

$$J(x)=g(d(x,boundary); \sigma), \quad (3)$$

where g(t) is a Gaussian function with standard deviation σ, and d(x, boundary) is the distance from the pixel x to the boundary of the target anatomical object. As described above in the landmark detection case, for each training image multiple ground truth Gaussian distributed probability maps are generated using different a values in order to generate a set of multi-scale ground truths for each training image.

Figure 10:
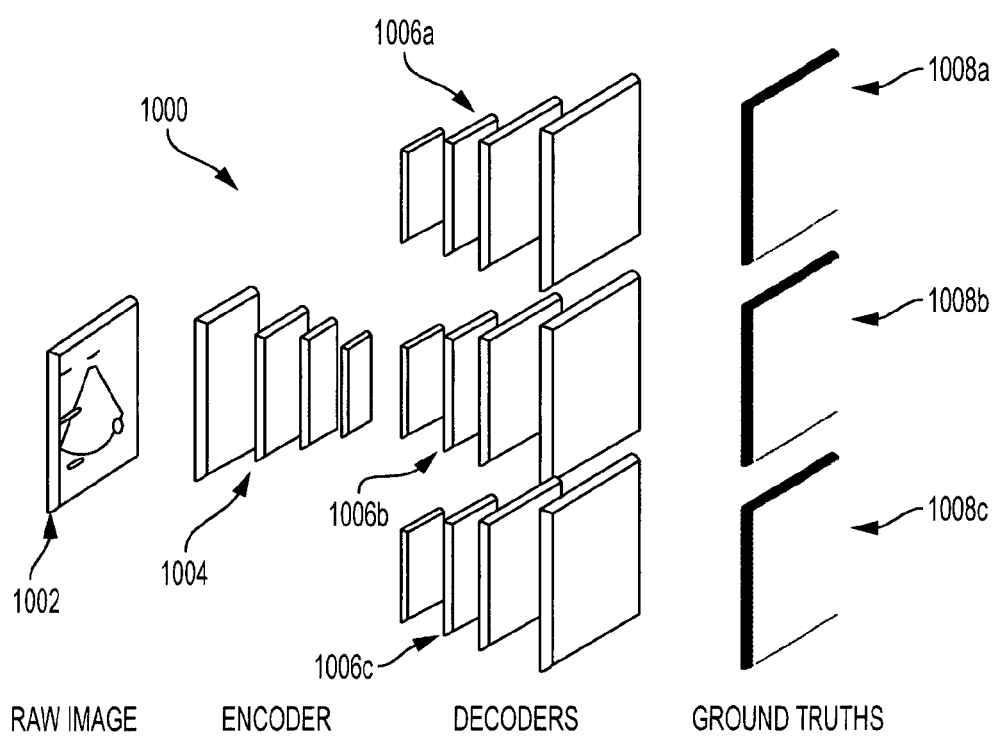
FIG. 10 illustrates an exemplary DI2IN that predicts multi-scale probability maps for an input medical image according to an embodiment of the present invention.

At step 906, a deep image-to-image network (DI2IN) is trained based on the multi-scale ground truths generated for the training images. According to an advantageous embodiment of the present invention, the DI2IN is trained based on the input training images and the multi-scale ground truth probability maps generated for each of the input training images to learning a mapping that predicts multi-scale probability maps from an input medical image. FIG. 10 illustrates an exemplary DI2IN 1000 that predicts multi-scale probability maps for an input medical image according to an embodiment of the present invention. As shown in FIG. 10, a common encoder 1004 is shared across all output scales, while multiple decoders 1006a, 1006b, and 1006c are used, with a respective decoder 1006a, 1006b, and 1006c for each scale of the ground truth probability maps 1008a, 1008b, and 1008c. For each training image the raw image 1002 is input to the encoder 1004. The output of the encoder 1004 is input to each of the decoders 1006a, 1006b, and 1006c, and each decoder 1006a, 1006b, and 1006c estimates a respective one of the multi-scale ground truth probability functions 1008a, 1008b, and 1008c. The loss function to be minimized in the training of the DI2IN 1000 can be considered as a summation of the loss from all of the decoders 1006a, 1006b, and 1006c. The loss for each decoder 1006a, 1006b, and 1006c is the error between the estimated probability map and the ground truth probability map at that scale (i.e., a value). The DI2IN 1000 can be trained in an end-to-end fashion using well-known back-propagation optimization methods to learn weights that minimize the loss function.

In a possible implementation, the DI2IN can be extended to handle detection of multiple landmarks in the same medical image. In this case, each landmark would have individual decoders for each scale, such that the total number of decoders is equal to the number of scales multiplied by the number of landmarks. The DI2IN can be similarly applied to segmentation of more than anatomical object in the same medical image. Once the DI2IN is trained, the DI2IN can be stored, for example in a memory or storage of a computer system and used to perform landmark detection or anatomical object segmentation is newly received/input medical images.

Returning to FIG. 9, steps 908-914 are used for online landmark detection or anatomical object segmentation in a newly received medical image. At step 908, a medical image of a patient is received. The medical image can be a 2D image, 3D image, or 4D (3D+time) image. The medical image can be acquired using any medical imaging modality, such as computed tomography (CT), magnetic resonance imaging (MRI), ultrasound, X-ray, DynaCT, positron emission tomography (PET), etc. The medical image may be received directly from an image acquisition device, such as a CT scanner, MRI scanner, ultrasound device, C-arm image acquisition device, etc., or may be received by loading a previously stored medical image from a memory or storage of a computer system or receiving the medical images in an electronic transmission from another computer system.

At step 910, Gaussian probability maps at multiple different scales are generated from the received medical image using the trained DI2IN. In particular, the received medical image of the patient is input to the trained DI2IN trained at step 906 (e.g., DI2IN 1000 of FIG. 10), and the trained DI2IN estimates multiple Gaussian probability maps at different scales from the input medical image. As described above, the multiple scales correspond to different a values for the Gaussian function.

At step 912, the Gaussian probability maps generated at the multiple scales from the received medical image are combined into a combined probability map. For example, the Gaussian probability maps generated at the multiple scales can be combined by multiplying the pixel probability values in the different probability maps together, adding the pixel probability values in the different probability maps together, or averaging the pixel probability values in the different probability maps.

At step 914, the target landmark is detected or the boundary of the target anatomical object is segmented in the received medical image based on the combined probability map. For landmark detection, the location of the target landmark can be detected at a location in the medical image corresponding to a location having a maximum value (probability) in the combined probability map. Similarly, for the detection of a segmented boundary in the medical image, each of the probability maps defines a Gaussian band that provides and estimate of the segmented boundary, and the segmented boundary of the target anatomical object can be detected as a set of points or band in the combined probability map having a maximum probability. Alternatively, the segmented boundary can be extracted by fitting a statistical shape model that maximizes the probability from the combined map. The detected landmark or the segmented boundary is then output, for example, by displaying the detected landmark or segmented boundary on a display device of a computer system.

The method of FIG. 9 is different from the classic multi-resolution coarse to fine strategy, where the detection is performed in a top-down manner (first at a lower resolution and then at a higher resolution) to prevent local minimum issues. The method of FIG. 9 considers multiple scales at the same time for both precision and robustness, and does not down-sample the original image, which may cause potential loss of important features. The method of FIG. 9 is also different from simple concatenation of multiple types of handcrafted features. For example, it has been proven effective to combine Haar-like features and steerable features to capture both position and orientation of a local area. The method of FIG. 9 implicitly learns the local appearance including but not limited to the local appearance represented by the handcrafted features, while the concatenation of multiple scales of ground truth is designed to capture the target-environment relationship at different scales of a region of interest to ensure precision and robustness.

Figure 11A:
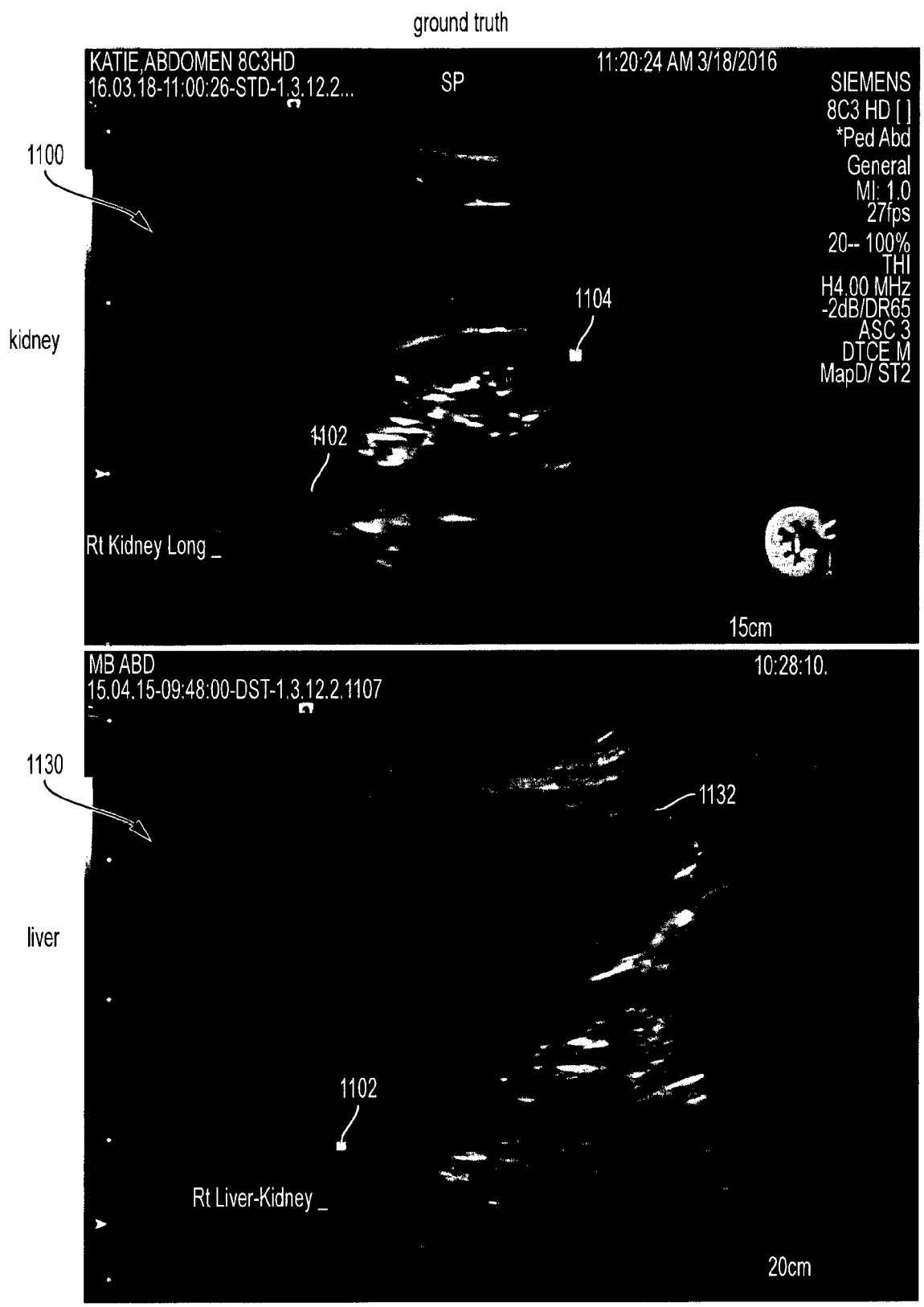
FIG. 11 illustrates exemplary landmark detection results in kidney and liver 2D ultrasound images.
Figure 11B:
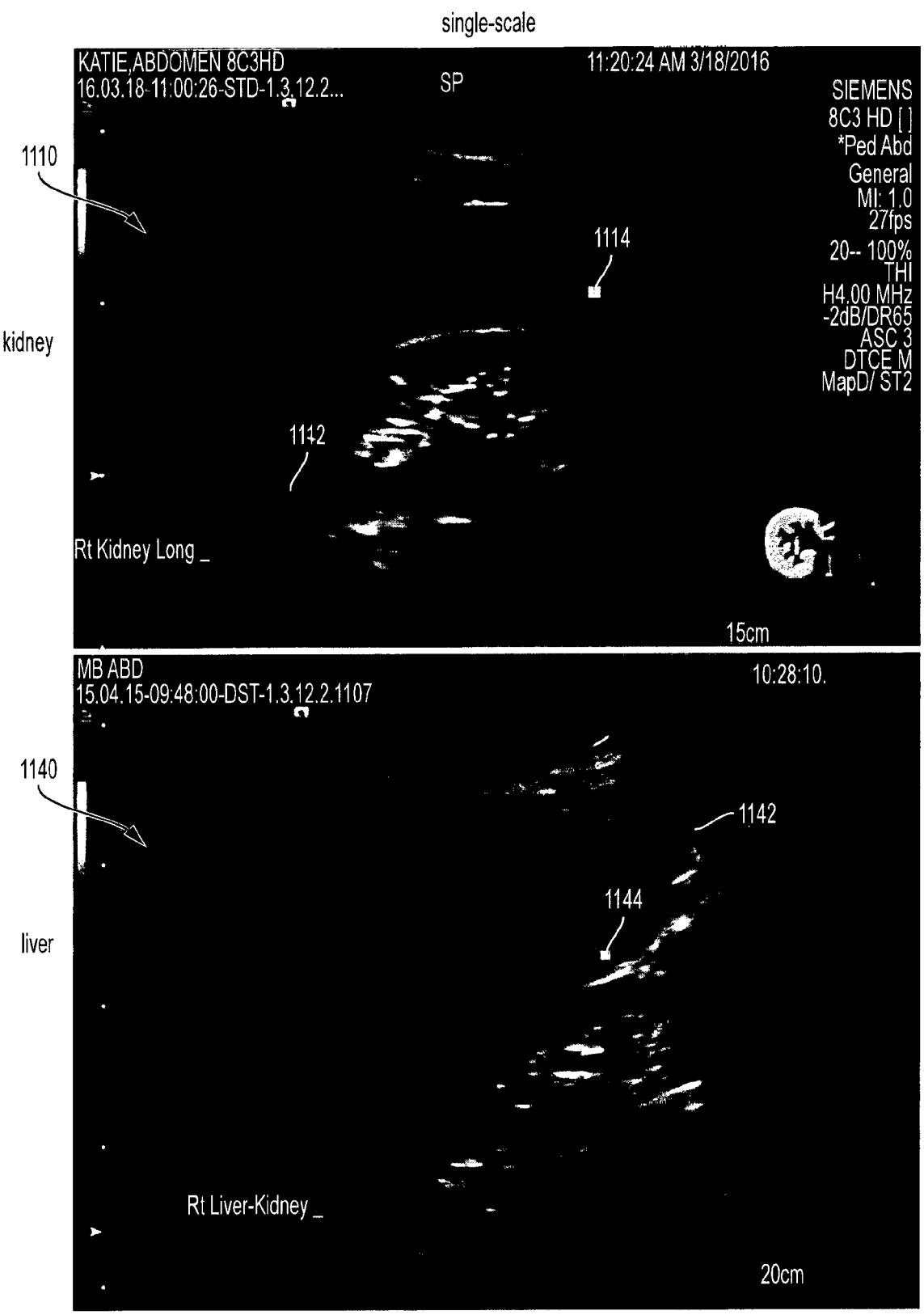
Figure 11C:
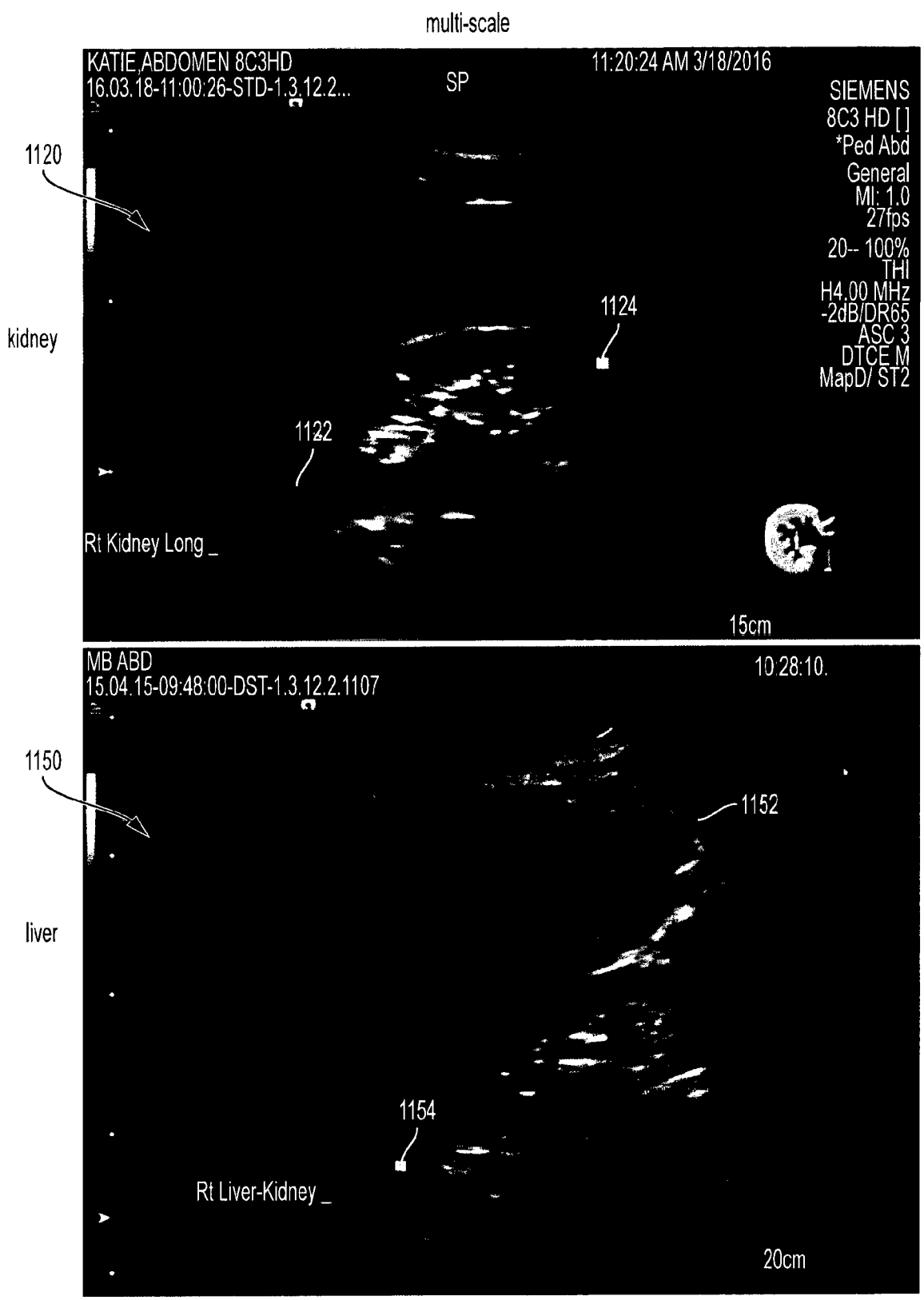

The present inventors applied to DI2IN landmark detection method of FIG. 9 to two 2D datasets: (1) 1081 kidney longitudinal ultrasound scans (627 training and 409 testing images); and (2) 356 liver longitudinal ultrasound scans (281 training and 75 testing images). There were two landmarks of interest in both datasets. The landmark detection using the DI2IN with multi-scale output images is compared to landmark detection using a single-scale counterpart (single decoder). FIG. 11 illustrates exemplary landmark detection results in kidney and liver 2D ultrasound images. As shown in FIG. 11, image 1100 shows ground truth locations for a first landmark 1102 and a second landmark 1104 in a 2D kidney longitudinal ultrasound image, image 1110 shows the detected location for the first landmark 1112 and the detected location for the second landmark 1114 in the 2D kidney longitudinal ultrasound image using the single-scale output, and image 1120 shows the detected location for the first landmark 1122 and the detected location for the second landmark 1124 in the 2D kidney longitudinal ultrasound image using the multi-scale outputs. Further, image 1130 shows ground truth locations for a first landmark 1132 and a second landmark 1134 in a 2D liver longitudinal ultrasound image, image 1140 shows the detected location for the first landmark 1142 and the detected location for the second landmark 1144 in the 2D liver longitudinal ultrasound image using the single-scale output, and image 1150 shows the detected location for the first landmark 1152 and the detected location for the second landmark 1154 in the 2D liver longitudinal ultrasound image using the multi-scale outputs. Table 2 shows distance errors (in mm) of landmark detection in the 2D kidney longitudinal views using the single-scale and multi-scale approaches. Table 2 shows distance errors (in mm) of landmark detection in the 2D liver longitudinal views using the single-scale and multi-scale approaches. As shown in Tables 2 and 3, the approach with multi-scale outputs results in less mean distance errors than the single-scale approach, and thus is more accurate, and also substantially decreases the maximum errors, and this is more robust.

TABLE 2

| Kidney | Landmark 1 | | Landmark2 | |
| --- | --- | --- | --- | --- |
| | mean | max | mean | max |
| Single-scale | 9.45 | 129.82 | 7.92 | 56.76 |
| Multi-scale | 8.14 | 66.11 | 7.19 | 37.98 |

TABLE 3

| Liver | Landmark 1 | | Landmark2 | |
| --- | --- | --- | --- | --- |
| | mean | max | mean | max |
| Single-scale | 13.17 | 152.50 | 15.33 | 180.79 |
| Multi-scale | 11.33 | 42.65 | 10.48 | 143.29 |

Robust Deep Learning Based Medical Image Segmentation with Partial Inference

This embodiment provides a method for deep learning based medical image segmentation with partial inference that can perform robust segmentation of an anatomical structure in a medical image even in the presence of domain shift. An application of this method to myocardium contouring in cardiac MR under domain shift it described herein, but this embodiment is not limited to myocardium contouring and can be similarly applied to perform other image segmentation tasks as well.

Machine learning based segmentation methods have been widely applied in medical image analytics with success, however, such machine learning based segmentation methods encounter great challenges where images at deployment present different distributions from those in training (i.e., domain shift), especially when no images at deployment are available at training. Cardiac magnetic resonance (CMR) is a powerful tool in both research and clinical practice. In a typical CMR exam, long-axis views such as two-chamber (2 ch), three-chamber (3 ch), and four-chamber (4 ch) views are acquired. These views are clinically defined, and are virtual planes cutting through the heart that are used to evaluate anatomy and functionality within and among various heart chambers and valves. Delineating the myocardium and tracing the endo- and epi-cardium border (i.e., contouring) from these long-axis views, together with other view analysis, is used to estimate important clinical parameters for diagnosis. Manual contouring requires extensive clinical expertise, is time-consuming, and is also error prone with significant intra- and inter-user variabilities. Therefore, fully automated myocardium contouring solution is highly desirable. In addition, it is important that the segmentation algorithm to perform the automated myocardium contouring keep the myocardium contours as a continuous entity.

Myocardium contouring has been addressed through traditional computer vision methods or machine learning based algorithms. However, these techniques are not designed to deal with domain shift, and performance decreases when images at deployment present different distributions and imaging artifacts due to different MR coil configurations and other factors. Without domain shift, a deep convolutional encoder-decoder (CED) can be used to generate segmentation results with excellent myocardium continuity. However, in the presence of domain shift, missing/broken segmented myocardium result are generated, resulting in extraction of diagnostically unacceptable myocardium contours.

According to an advantageous embodiment of the present invention, in order to tackle the challenge of domain shift without any deployment data available at training, deep learning is used to learn a hierarchical model to infer the full segmentation of a target anatomical structure from partial segmentation results, where the partial segmentation results can be obtained by conventional learning-based approaches such as a deep CED, thanks to small overlaps between deployment and training distributions. According to an advantageous embodiment, as no deployment data is available at the learning/training stage, partial segmentation results are synthesized from the available training data. Together with the original medical image, a joint tensor representation is constructed to combine the original image and the partial segmentation results, and deep learning is used to learn a mapping between this joint tensor representation and the target segmentation mask. The trained deep learning model is iteratively applied to progressively improve the segmentation results. Once the mask at convergence is obtained, contours are extracted. The method described herein provides robust segmentation in the presence of domain shift. For example due to the diversity and flexibility of MR, it is often the case that the deployment and training present different image distributions. Furthermore, even when domain shift is not present, the two-stage segmentation method described herein boost robustness in its component deep-learning based algorithm.

Figure 12:
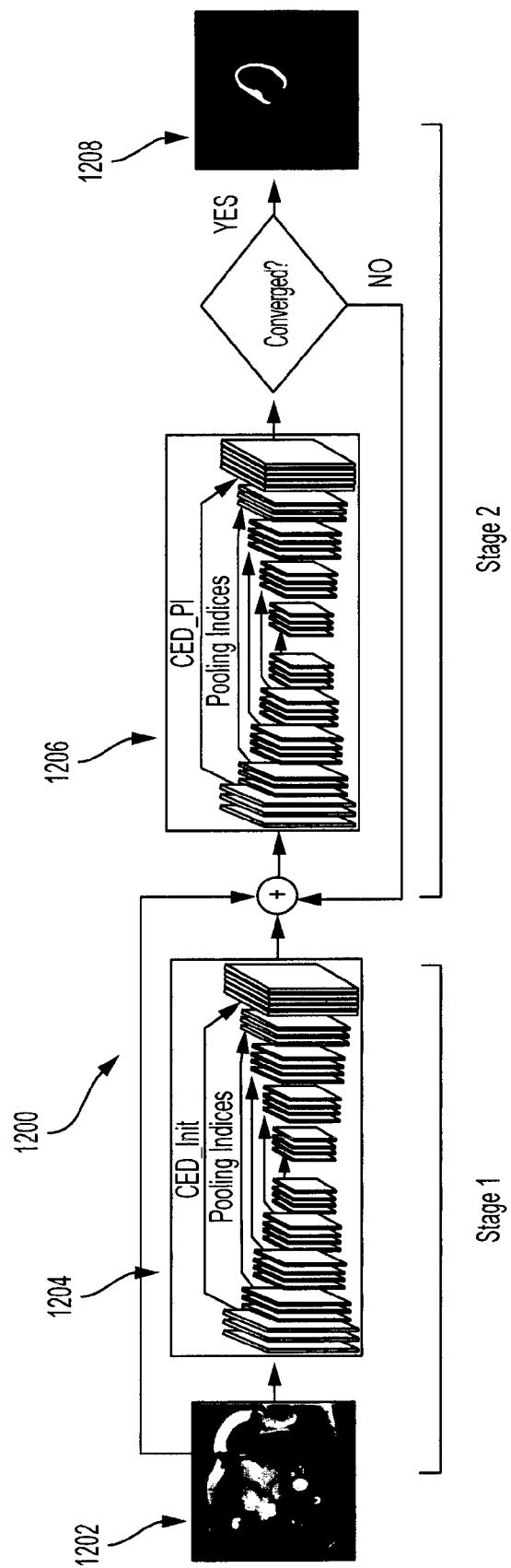
FIG. 12 illustrates a framework for deep learning partial inference based medical image segmentation according to an embodiment of the present invention.

FIG. 12 illustrates a framework for deep learning partial inference based medical image segmentation according to an embodiment of the present invention. As shown in FIG. 12, the segmentation framework 1200 performs medical image segmentation in a two stage workflow. In the first stage (Stage 1), a first deep convolutional encoder decoder (CED) 1204 is used to learn a mapping from an input medical image 1202 (e.g., MR image) to a segmentation mask. The first deep CED 1204 is referred to herein as the initial CED (CED_Init). In the second stage (Stage 2), a multi-channel representation is used to embed the input medical image 1202 and the previous segmentation results into a unified tensor, which is fed into a second deep CED 1206 to generate an updated segmentation mask. The second CED 1206 is referred to herein as the partial inference CED (CED_PI). The second stage is applied in an iterative fashion in which the updated segmentation mask generated by CED_PI 1206 is iteratively combined with the input image 1202 to generate a new tensor input that is input to CED_PI 1206 to generated a new updated segmentation mask until the updated segmentation masks generated by CED_PI 1206 converge. Once the updated segmentation masks generated by CED_PI 1206 converge, the final segmentation mask 1208 is output, and can be used to extract contours from the original input image 1202.

According to an advantageous embodiment, the deep CED learning architecture can be used to learn an end-to-end pixel-wise labeling model at both stages. The strengths of the CED model include its great modeling capacity from a large annotated training image set and its built in regularization mechanism, both due to the deep hierarchical feature network representation and pooling-upsampling structures. The flexibility of the CED's tensor input structure is leverage in the framework 1200 of FIG. 12. In the first stage, an image (1202) is used as the input to CED_Init 1204. In the second stage, a combined image/partial-segmentation mask is fed into CED_PI 1206. The output of both CEDs 1204 and 1206 is a segmentation mask. In an advantageous implementation, in both CEDs 1204 and 1206, except for the input layer, all other layers share the same structures. In particular, as shown in FIG. 12, in both CED_Init 1204 and CE_PI 1206, five convolutional layers and followed by five deconvolutional layers. Although the CED architecture is used in an advantageous embodiment and illustrated in FIG. 12, the present invention is not limited thereto and other deep learning architectures can be used as well.

Figure 13:
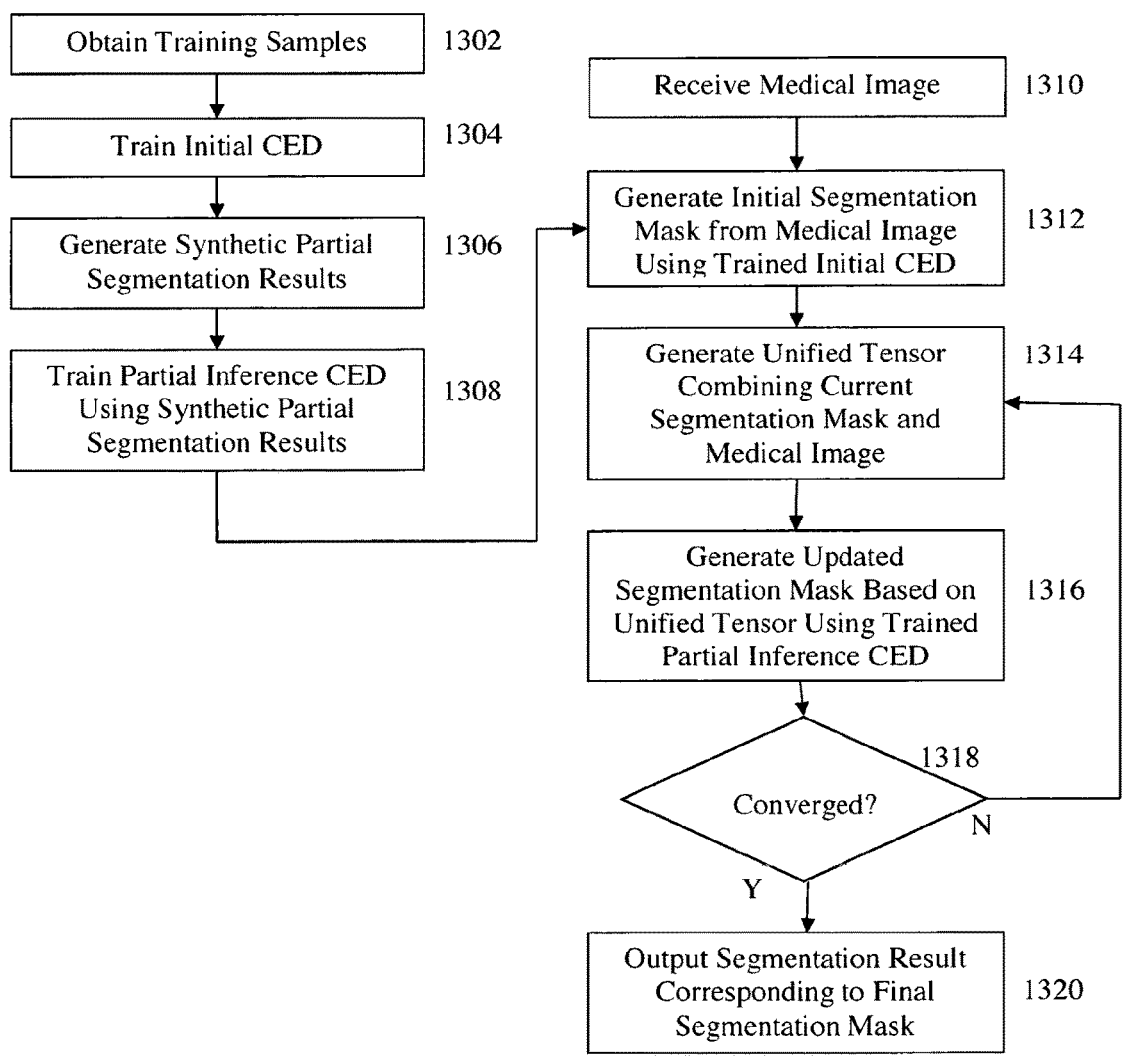
FIG. 13 illustrates a method for deep learning partial inference based medical image segmentation according to an embodiment of the present invention.

FIG. 13 illustrates a method for deep learning partial inference based medical image segmentation according to an embodiment of the present invention. The method of FIG. 13 illustrates method steps/operations to implement the framework illustrated in FIG. 12. Steps 1302-1308 of FIG. 13 are a training phase that are performed offline to train initial CED (CED_Init) and the partial inference CED (CED_PI) prior to actual online deployment for performing segmentation of an anatomical structure in a newly received medical image.

At step 1302, training samples are obtained. Each training sample is a training image-segmentation mask pair. The training images are medical images and the segmentation masks provides the ground truth segmentations for a target anatomical object in the corresponding training images. The training samples may be obtained by loading existing training images with ground truth segmentations of the target anatomical structure from a database. Alternatively, medical images without known ground truth annotations can be loaded from a database or acquired from a medical image acquisition device and manually annotated to generate training samples.

At step 1304, the initial CED (CED_Init) is trained based on the training samples. The initial CED can have a CED structure of five convolutional layers, followed by five de-convolutional layers, as shown in FIG. 12, but the present invention is not limited thereto. The initial CED is trained based on the training samples to learn an end-to-end pixel-wise model that best maps the training images to the corresponding ground truth segmentation masks. The initial CED can be trained using well known back-propagation optimization methods to learn weights that minimize a loss function calculated as a difference/error between the estimated segmentation maps and the ground truth segmentation maps over the set of training samples.

At step 1306, synthetic partial segmentation results are generated from the training samples. In clinical applications, especially in MR (but not limited thereto), images at deployment may present different intensity distributions from those in training, resulting in domain shift. For medical image segmentation applications in imaging modalities subject to domain shift, such as myocardium segmentation in CMR images, a miss rate (i.e., classifying the target structure as background) of convention CED significantly increases under domain shift, leading to partial segmentation of the target structure. According to an advantageous embodiment, to infer complete segmentation results of a target structure form such partial segmentation, a large set of synthesized data can be generated to represent such partial segmentation results and used to train the partial inference CED (CE_PI). In an advantageous implementation, for each training image-segmentation pair, the ground truth segmentation mask can be partially knocked out at random to synthesize partial segmentation results. That is, a plurality of synthetic partial segmentation results can be generated from each ground truth segmentation mask by randomly removing different portions of the ground truth segmentation result in each segmentation mask. If it is known a priori which image regions tend to different intensity distributions, the synthesis process can be more focused on those regions, which may lead to convergence of the online iterative updates.

Figure 14:
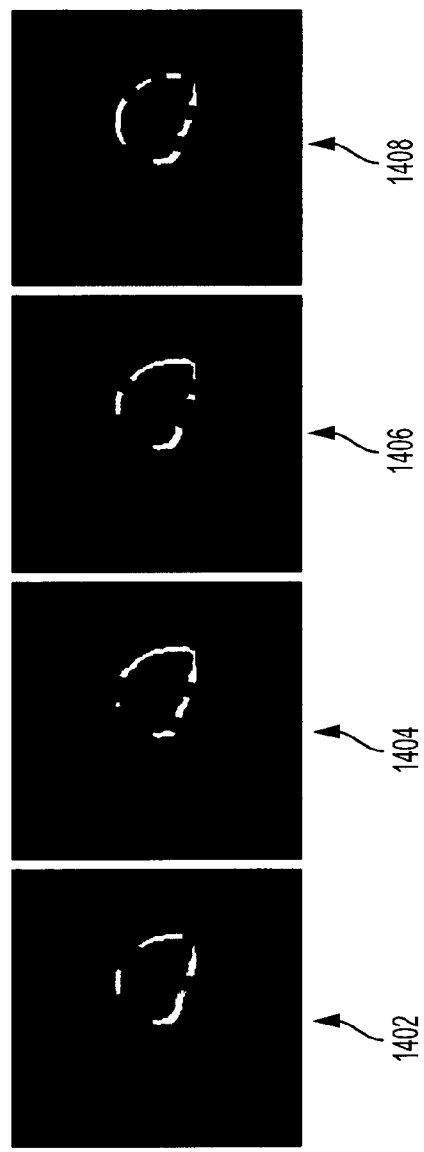
FIG. 14 illustrates exemplary synthesized partial myocardium segmentation results.

In an exemplary application of myocardium segmentation in CMR images, the synthetic partial segmentation results can be generated as follows. For each original training sample (i.e., image/mask pair), the myocardium skeleton is extracted and n (e.g., n=5) seed points are selected along the myocardium skeleton at random. Portions from the full myocardium mask are then knocked-out using a disk with a pre-defined radius and centered at each seed point. This can be performed multiple times for each original training sample to generate multiple different randomly selected partial segmentation results from each original training sample. FIG. 14 illustrates exemplary synthesized partial myocardium segmentation results. As shown in FIG. 14, images 1402, 1404, 1406, and 1408 show synthesized partial segmentation masks generated by removing portions from ground truth myocardium segmentation masks for training CMR images.

Returning to FIG. 13, at step 1308, the partial inference CED (CED_PI) is trained using the synthetic partial segmentation results. The partial inference CED can have a CED structure of five convolutional layers, followed by five de-convolutional layers, as shown in FIG. 12, but the present invention is not limited thereto. The partial inference CED is trained using the synthesized partial segmentation results. Each of the synthesized partial segmentation result is used as a training sample for training the partial inference CED, along with the corresponding original training image and original ground truth segmentation mask. For each such training sample, the original training image and the synthesized partial segmentation mask are combined into a unified tensor that is input to the partial inference CED, and the partial inference CED is trained to learn an end-to-end pixel-wise model that best maps the unified tensors for the training samples to the corresponding ground truth segmentation masks. The partial inference CED can be trained using well known back-propagation optimization methods to learn weights that minimize a loss function calculated as a difference/error between the segmentation maps estimated based on the training image/partial segmentation mask tensor and the ground truth segmentation maps over the set of training samples.

Steps 1310-1320 are an online deployment phase, in which the trained initial CED and trained partial inference CED are deployed to perform segmentation of a target anatomical structure in newly received medical images. At step 1310, a medical image of a patient is received. The medical image can be a 2D image, 3D image, or 4D (3D+time) image. The medical image can be acquired using any medical imaging modality, such as computed tomography (CT), magnetic resonance imaging (MRI), ultrasound, X-ray, DynaCT, positron emission tomography (PET), etc. The medical image may be received directly from an image acquisition device, such as a CT scanner, MRI scanner, ultrasound device, C-arm image acquisition device, etc., or may be received by loading a previously stored medical image from a memory or storage of a computer system or receiving the medical images in an electronic transmission from another computer system.

At step 1312, an initial segmentation mask is generated from the medical image using the trained initial CED. The trained initial CED inputs the received medical image and performs a pixel-wise mapping on the input medical image to generate the initial segmentation mask. The initial segmentation mask may be a partial segmentation mask.

At step 1314, the current segmentation mask is combined with the original received medical image to generate a unified tensor. In particular, a multi-channel representation can be used to embed the original received medical image and the current segmentation mask into the unified tensor. The first time the method performs step 1314, the current segmentation mask is the initial segmentation mask generated by the initial CED. Each subsequent time that step 1314 is repeated, the current segmentation mask is the updated segmentation mask generated by the partial inference CED in the most recent iteration.

At step 1316, an updated segmentation mask is generated based on the unified tensor using the trained partial inference CED. The trained partial inference CED inputs the unified tensor, which combines the original received medical image and the current segmentation mask using a multi-channel representation, and performs a pixel wise mapping on the unified tensor to generate an updated segmentation mask.

At step 1318, it is determined if the updated segmentation mask has converged. In particular, an error value can be calculated between the updated segmentation mask and the previously generated segmentation mask. If the error value is less than a predetermined threshold, it is determined that the updated segmentation mask has converged. If the updated segmentation mask has not yet converged, the method returns to step 1314. During training of the partial inference CED, the synthesis of partial segmentation results used to train the partial inference CED will typically not cover all variations of possible partial segmentation results. Accordingly, at the online inference stage on unseen data (e.g., the received medical image), inference of a segmentation mask by the partial inference CED may not lead to the global target with one prediction. Accordingly, iterative updates of the segmentation mask using the partial inference CED are performed (step 1316) and after each update the updated segmentation mask is combined with the original image as a new unified tensor (step 1314) and input into the partial inference CED for further improvement until the updated segmentation mask converges. When it is determined that the updated segmentation mask has converged, the latest updated segmentation mask is determine to be the final segmentation mask, and the method proceeds to step 1320.

At step 1320, the segmentation result corresponding to the final segmentation mask is output. In particular, the final segmentation mask is applied to the original received medical image to segment the target anatomical structure from the received medical image. The segmentation result can be output, for example, by displaying the segmentation result on a display device of a computer system.

Figure 15:
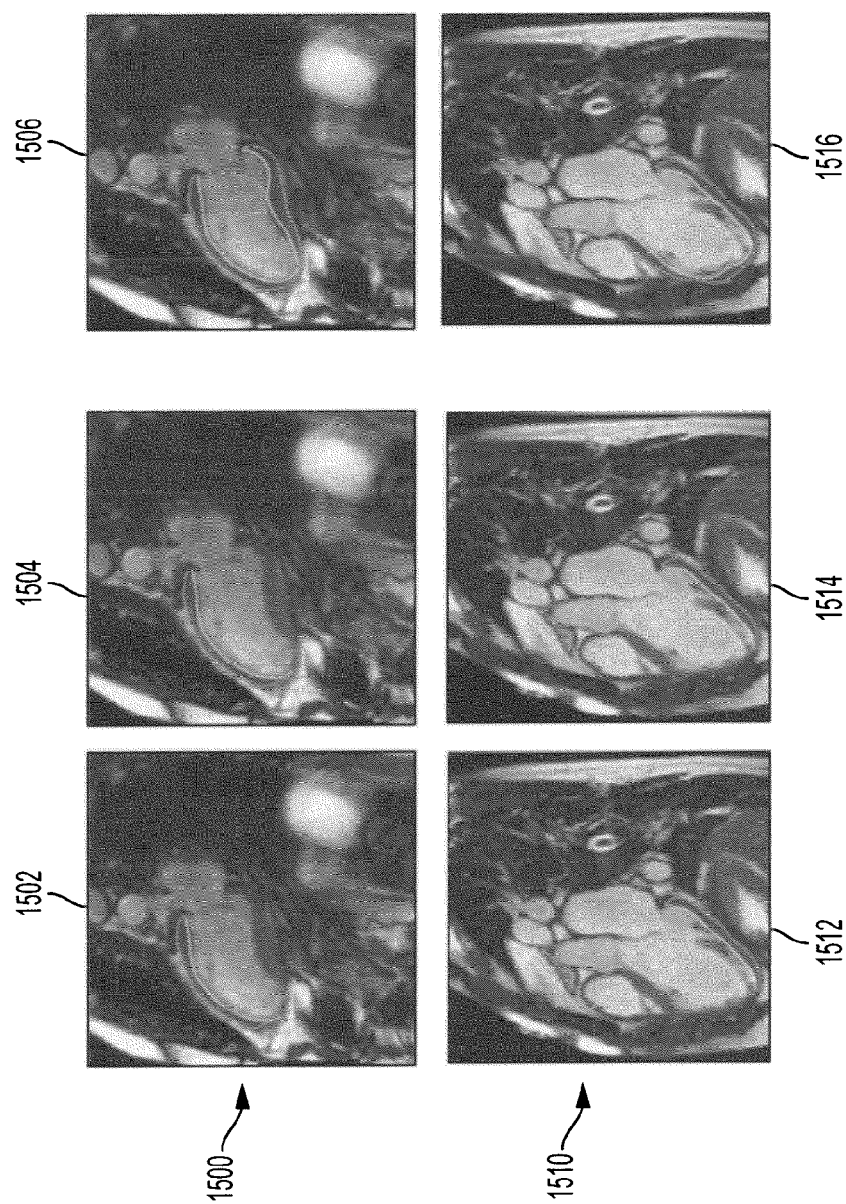
FIG. 15 illustrates examples of progressive segmentation results for myocardium segmentation in CMR images using the method of FIG. 13.

FIG. 15 illustrates examples of progressive segmentation results for myocardium segmentation in CMR images using the method of FIG. 13. As shown in FIG. 15, row 1500 illustrates exemplary progressive segmentation results for myocardium segmentation in a first CMR image. Segmentation result 1502 is an initial segmentation of the myocardium in the first CMR image based on the initial segmentation mask generated by the trained initial CED. Segmentation result 1504 is a segmentation of the myocardium in the first CMR image based on the updated segmentation mask generated after one iteration with the trained partial inference CED. Segmentation result 1506 is the final segmentation of the myocardium in the first CMR image based on the final converged segmentation map generated by the trained partial inference CED. Row 1510 illustrates exemplary progressive segmentation results for myocardium segmentation in a second CMR image. Segmentation result 1512 is an initial segmentation of the myocardium in the second CMR image based on the initial segmentation mask generated by the trained initial CED. Segmentation result 1504 is a segmentation of the myocardium in the second CMR image based on the updated segmentation mask generated after one iteration with the trained partial inference CED. Segmentation result 1506 is the final segmentation of the myocardium in the second CMR image based on the final converged segmentation map generated by the trained partial inference CED.

In an advantageous embodiment, in which the method of FIG. 13 is used for CMR long-axis myocardium contouring, once the progressive segmentation is finished, endo-myocardium and epi-myocardium contours can be calculated from the final segmentation mask as follows. First, the largest connected component is selected as the final myocardium segmentation result. The centroid of the segmentation mask is then calculated to determine a point within the left ventricle blood pool. Boundary points surrounding the mask are then computed, and two turning points at the left ventricle base are detected based on the point determined to be within the left ventricle blood pool. The boundary points are then partitioned and traced to generate the endo-myocardium and epi-myocardium contours.

The present inventors performed benchmark testing of the method of FIG. 13 for myocardium segmentation in CMR images. 3983 images were used for training and 256 images were used for testing. If disjoint segments were observed in the automatic segmentation result, the segmentation was considered clinically unacceptable and determined to be a failure. Segmentation using a conventional single-stage CED resulted in a failure rate of 14%. Segmentation using the method of FIG. 13 reduced the failure rate to 4%.

Fitting an Active Shape Model to a Medical Image Using a Recurrent Neural Network The active shape model (ASM) is a well-known method for modeling a deformable shape and fitting it to an image. ASM is widely using in medical image analysis. The conventional ASM method, although widely used, has some limitations. This embodiment addresses limitations of the conventional ASM method using a deep learning, and in particular, a recurrent neural network (RNN) architecture.

ASM assumes that a deformable shape S is represented by a set of points $S=[p_0, p_1, \ldots, p_n]$ and is decomposed into a linear combination: $S=S_0+\Sigma_k \alpha_k S_k$, in which $S_0$ is the mean shape and $\{S_k\}$'s are eigenshapes derived from a principal component analysis (PCA). Ideally S could be fit directly to image I by maximizing a certain cost function $C(S|I)$:

$$S = \mathrm{argmax}_S C(S|I) = \mathrm{argmax}\ C(\{\alpha_k\}|I).$$

However, since $\{\alpha_k\}$ is high-dimensional, direct optimization is challenging. Hence the optimization is broken into two steps: Step 1) For each point $p_i$ on the current shape $S=[p_0, p_1, \ldots, p_n]$, independently search along its normal line for a local maximal location $p'_i$; and Step 2) Project the new shape $S'=[p'_0, p'_1, \ldots, p'_n]$ into the PCA shape space to obtain a new shape. Steps 1 and 2 are repeated until convergence or a maximal number of iterations is reached. Sometimes (particularly in the last few iterations), step 2 may be replaced by a simple smoothing operation to better preserve the shape or avoid over-constraint posed by the ASM.

The accuracy of fitting the ASM to an image largely depends on the performances of both steps. Step 1 concerns the relationship between the shape and the image, and step 2 is related to the statistical shape model learned for the target structure. In step 1, there are two main components that affect the performance: (a) independent normal line search; and (b) the maximizing score function $C(p|I)$. The limitation in (a) lies in that the search is done independently. In (b), the score function needs to be determined. The more effective the score function, the better the performance of step 1 and the overall accuracy of the ASM. In step 2, the statistical shape model is given by the PCA analysis and its quality is governed by the training shapes used to learn the PCA shape space.

While there are different techniques that can be used to increase the modeling power of a shape model, for example by using non-linear PCA, etc., this embodiment addresses limitations related to step 1 of the conventional ASM method. To increase the maximizing power of the score function $(p|I)$, machine learning methods can be used in practice. For example, a discriminative classifier $(p|I)=Pr(+1|I[p])$ can be trained using a support vector machine (SVM) or probabilistic boosting tree (PBT). However, there is no known method to address the independence in the normal line search.

Figure 16:
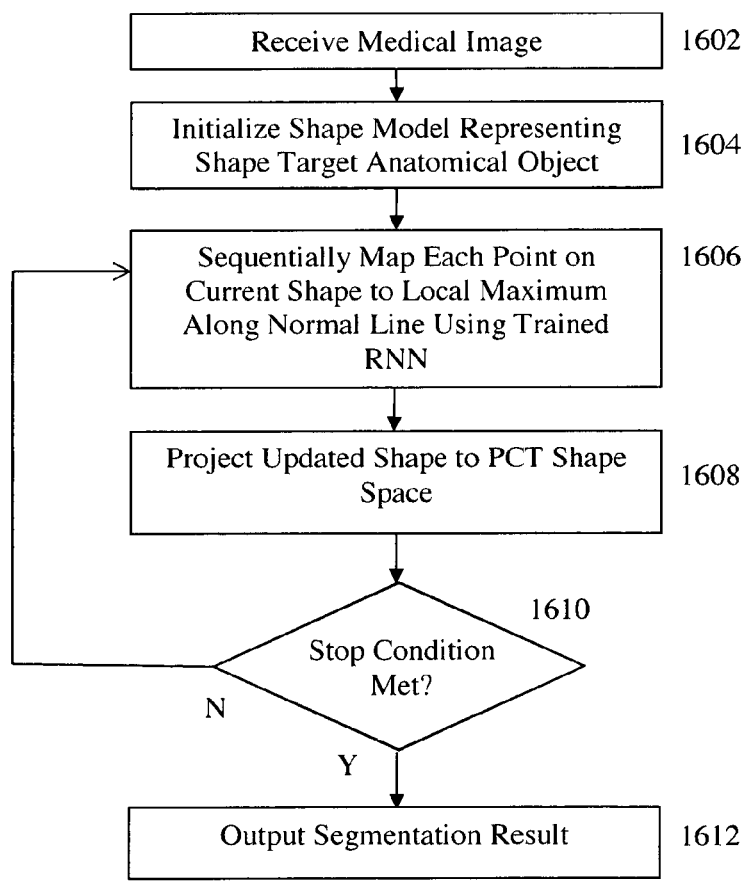
FIG. 16 illustrates a method of fitting an active shape model (ASM) to a medical image to segment a target anatomical structure according to an embodiment of the present invention.

In an advantageous embodiment of the present invention, a recurrent neural network (RNN) is used to increase the performance of step 1 of the ASM method. FIG. 16 illustrates a method of fitting an ASM to a medical image to segment a target anatomical structure according to an embodiment of the present invention. The method of FIG. 16 is similar to the ASM method described above, but instead of using conventional techniques for implementing search for the normal line for the maximal location for each point on the shape, the method of FIG. 16 uses a trained RNN to sequentially map each point on the current shape to a local maximum along the normal line (step 1606).

Referring to FIG. 16, at step 1602, a medical image of a patient is received. The medical image can be a 2D image, 3D image, or 4D (3D+time) image. The medical image can be acquired using any medical imaging modality, such as computed tomography (CT), magnetic resonance imaging (MRI), ultrasound, X-ray, DynaCT, positron emission tomography (PET), etc. The medical image may be received directly from an image acquisition device, such as a CT scanner, MRI scanner, ultrasound device, C-arm image acquisition device, etc., or may be received by loading a previously stored medical image from a memory or storage of a computer system or receiving the medical images in an electronic transmission from another computer system.

At step 1604, a shape model representing the shape of a target anatomical object in the medical image is initialized. The shape model can be a statistical shape generated using PCA based on a large number of shapes of the target anatomical object in training data. In a possible implementation, the shape model can be initialized in the medical image as the mean shape of the target anatomical object learned from the training data. The location/pose of the shape model in the medical image can be determined automatically by an object localization algorithm (e.g., marginal space learning (MSL)) or can be determined based on user input.

At step 1606, each point on the current shape is sequentially mapped to a local maximum point along a normal line using a trained RNN. RNNs have typically been used for prediction tasks from sequential information with multiple time points. According to an advantageous embodiment, instead of regarding the points on shape $S=[p_0, p_1, \ldots, p_n]$ as spatial locations, the RNN treats them in a sequential order to learn a mapping with the target output $[y_0, y_1, \ldots, y_n]$, in which $y_i$ is defined as a signed distance function between the current location $p_i$ and it ground truth location.

Figure 17:
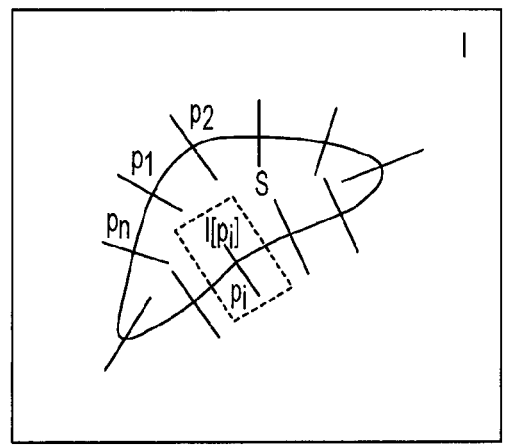
FIG. 17 illustrates an exemplary shape of a target anatomical structure in an image.
Figure 18:
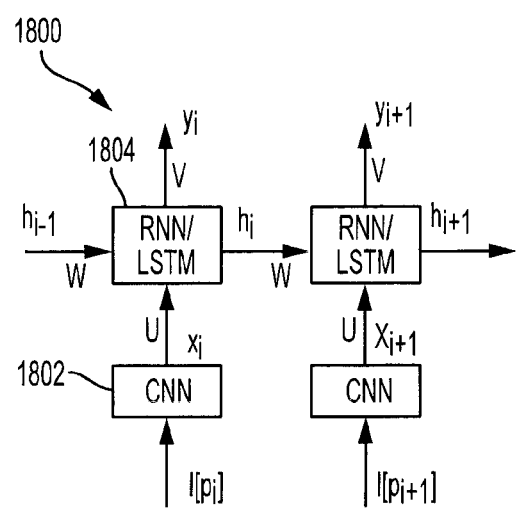
FIG. 18 illustrates an exemplary RNN architecture.

FIG. 17 illustrates an exemplary shape Sofa target anatomical structure in an image I. As shown in FIG. 17, the shape S has points $[p_0, p_1, \ldots, p_n]$. As the shape S has no particular beginning or end, the sequential order of the points $[p_0, p_1, \ldots, p_n]$ on the current shape S is artificially determined. For example, a starting point can be randomly selected from the points on the current shape and the RNN can then process the points sequentially starting with the randomly selected starting point and proceeding (in either direction) to each adjacent point around the shape. FIG. 18 illustrates an exemplary RNN architecture 1800. The RNN architecture 1800 of FIG. 18 includes a convolutional neural network (CNN) 1802 and an RNN/long short-term memory (LSTM) network 1804.

Referring to FIGS. 17 and 18, for a current point $p_i$, an image patch $I[p_i]$ that is aligned with its normal direction (i.e., normal to the shape S at the location of $p_i$) is extracted from the image I. The image patch $I[p_i]$ can be a patch having a predetermined size. The image patch $I[p_i]$ extracted at point $p_i$ is input to the CNN 1802 which extracts image features $x_i$ from the image patch $I[p_i]$. The image features $x_i$ are input to the RNN/LSTM 1804, which calculates a current hidden state $h_i$ and the output signed distance $y_i$ that maps the point $p_i$ to a new (optimal) location $p'_i$ along it normal line. In the RNN/LSTM 1804, the hidden state $h_i$ is a function of both the image feature and its previous hidden state $h_{i-1}$ (unless point $p_i$ is the first point in the sequential order and there is no previous hidden state $h_{i-1}$), and the output signed distance $y_i$ is calculated as a function of the hidden state $h_i$:

$$h_i = \Phi(Ux_i + Wh_{i-1})$$

$$y_i = \Psi(Vh_i).$$

In the above equations, U, W, and V are weights learned in training of the RNN/LSTM 1804 and $\Phi$ and $\Psi$ are non-linear operators. The above described operations are sequentially repeated for each point on the shape S to sequentially map each point to a new location along its normal line. In an alternative implementation, two trained LSTMs can be used, one that evaluates the points in the originally selected sequential order and another that evaluates the points in the reverse order, in order to form a bi-direction LSTM to compensate for arbitrariness in the ordering.

Although a CNN 1802 is used to extract the image features $x_i$ in the example of FIG. 18, a fully connected layer could be used instead of a CNN in an alternative implementation. Various kinds of RNN architectures have been proposed, such as LSTM and gated recurrent unit. It is to be understood that any type of RNN architecture can be used with any number of recurrent layers. The CNN (or fully connected layer) and the RNN are trained in an offline training phase based on annotated training data with known ground truth target locations.

The use of the RNN to map the points on the shape to new locations in step 1606 addresses both issues that arise in step 1 of the conventional ASM method. As described above, the mapping of a point on the shape to a new location by the RNN depends not only on the image patch extracted at that point, but also on the image patches extracted at other points as well. Accordingly, the recurrent part of the RNN addresses the independence limitation that arises in conventional techniques for performing step 1 of the ASM method. Furthermore, the deep neural network (i.e., the CNN or fully connected layer) used to extract the image features increases the discriminative power of the score function.

Returning to FIG. 16, at step 1608, the updated shape is projected to the learned PCT shape space of the target anatomical object. This can be performed as in other well-known ASM methods. At step 1610, it is determined whether a stop condition is met. For example, it can be determined whether the shape has converged or whether a maximal number of iterations has been reached. If the stop condition has not been met, the method returns to step 1606 and repeats steps 1606-1610 until the stop condition is met. In a possible implementation, step 1610 may be replaced in some iterations (particularly in the last few iterations) by a simple smoothing operation. When the stop condition (e.g., convergence or maximal number of iterations) is met, the method proceeds to step 1612. At step 1612, the segmentation result is output. The final shape is fitted to the medical image and represents the shape of the target anatomical object in the medical image. The segmentation result can be output, for example, by displaying the segmentation result corresponding final shape of the target anatomical object in the medical image on a display device of a computer system.

Training a Convolutional Neural Network from a Small-Size Database of Images Using Transfer Learning with Feature-Level Supervision Machine learning for medical image analysis is often used for segmentation of anatomical structures, as well as for other tasks, such as classification or recognition, object/anatomy detection, etc. Many deep learning based algorithms for medical image segmentation, and other medical image analysis tasks, utilize convolutional neural networks (CNNs). While learning a CNN from a large-size database of medical images (e.g., millions of images) has made significant progress in recent years, effective learning of a CNN from a small-size database of medical images (e.g., thousands or even hundreds of images) remains an unsolved challenge.

This embodiment provides and method for training a CNN using transfer learning with feature-level supervision that can effectively train a CNN from a small-size database of medical images. The method described herein can be used for training a CNN in any of the above described segmentation methods in which a CNN is used. The method described herein can also be used for other medical image analysis tasks that utilize a CNN, as well.

Currently in many medical image analysis tasks, the amount of medical image datasets available for training is scarce due to cost, privacy concerns, etc. Further, quality data annotations of these datasets necessary for training can be difficult to obtain. These factors often result in the number of medical image datasets available for training being measured in the thousands or hundreds, which leads to difficulty in training deep neural networks, such as CNNs. When training a CNN from a small-sized database, the learned model may be prone to overfit the training data. That is, while the training error is close to zero, the testing error is large. Even with a shallow network, which has sufficient modeling capacity, such overfitting may not diminish. It is therefore necessary to "regularize" the network so that the network does not overfit the training datasets.

One regularization approach is to perform transfer learning. In transfer learning, an already well-trained network that was trained based on a large-size database of medical images from a first domain ("domain A") is applied to a new problem with a small-sized database of medical images from a second domain ("domain B"). For example, CNN networks trained based on ImageNet, such as AlexNet, VGG-Net, etc., are often well learned. Such as well-trained CNN trained on large database of medical images from domain A is referred to herein as "CNN-A". There two types of transfer learning approaches that are typically used. In a first type of transfer learning approach, CNN-A is used as a fixed feature extractor. This is done by removing the last fully-connected layer(s) and taking the feature values from the intermediate layers as a fixed feature extractor for the new dataset. These features are then fed into other machine learning methods (e.g., support vector machine (SVM), boosting, etc.) for final decisions. Variants of this approach include using only the features from one intermediate layer or aggregating features from all intermediate layers. Further, feature selection can be applied before feeding the features into other machine learning methods. In a second type of transfer learning approach, CNN-A is fine tuned. This is done by retraining CNN-A using the small-size database of medical images from domain B, with the previously trained weights of CNN-A used for initialization. Also, it is possible to keep earlier layers fixed (due to overfitting concerns) and only fine-tune the remaining layers. This is motivated by the observation that the earlier features of CNN-A are more generic, like edge detectors or blob detectors, and hence useful to many tasks, but features of the later layers of CNN-A become progressively more specific to the details of domain A, which should be adapted to domain A.

One common limitation of the two transfer learning approaches described above is that the CNN-A network architecture is used for feature extraction. In the first approach, even the weights of CNN-A are kept the same, while in the second approach different weights are used. During the testing phase, the amount of time needed for feature computation is typically quite involved, as CNN-A is often very deep with many layers and millions of weights.

The embodiment described herein provides a transfer learning method that uses a different regularization strategy, referred to herein as feature level supervision (FLS). According to an advantageous embodiment, this transfer learning method can be used to effectively train a shallow network, rather than use the original network architecture of CNN-A. This transfer learning method outperforms other transfer learning approaches and is also computationally more efficient. In addition, the transfer learning method described herein can be applied across a hierarchy of domains while maintaining accuracy better than other transfer learning techniques.

Figure 19:
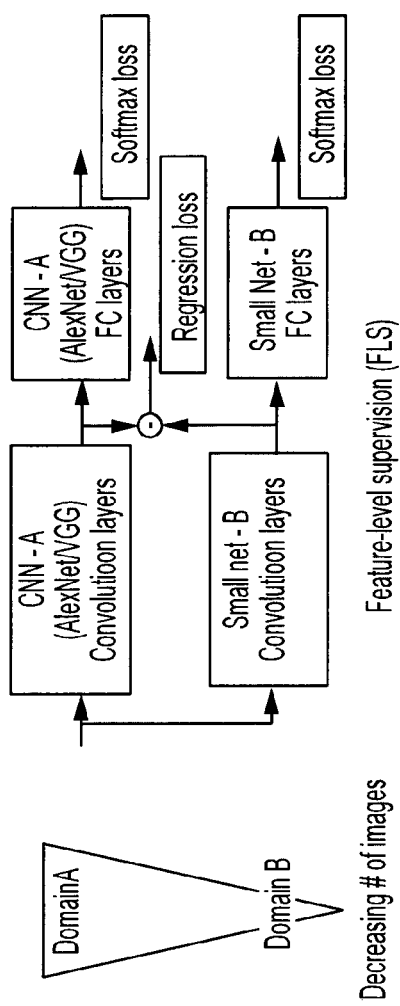
FIG. 19 illustrates a framework for feature-level supervision transfer learning according to an embodiment of the present invention.

FIG. 19 illustrates a framework for feature-level supervision transfer learning according to an embodiment of the present invention. The framework shown in FIG. 19 applies the feature-level supervision transfer learning to a medical image classification task, but could be similarly applied to perform medical image segmentation, or other medical image analysis tasks such as regression, ranking, registration, etc. As shown in FIG. 19, domain A includes a large database of medical images for training and domain B includes smaller-sized database of medical images for training than domain A. CNN-A is a CNN trained from training medical images in domain A. It is assumed that CNN-A is an existing well-trained network for domain A. The CNN-A network includes two parts: the convolutional layers that encode the input image into features, and the fully connected (FC) layers that convert the features for the final outcome (e.g., classification results, segment results, etc.). The goal of the feature-level supervision transfer learning is to train a second CNN, potentially of a smaller size than CNN-A, to perform a medical image processing task (e.g., classification, segmentation, etc.) for domain B, which possesses a small-size database of medical images. As shown in FIG. 19, the second CNN trained for domain B is referred to as "Small net-B". Small net-B is a CNN with a smaller architecture than CNN-A (e.g., fewer layers and/or weights), and the Small net-B network includes convolutional layers that encode the input image into features and FC layers that convert the features for the final outcome.

Figure 20:
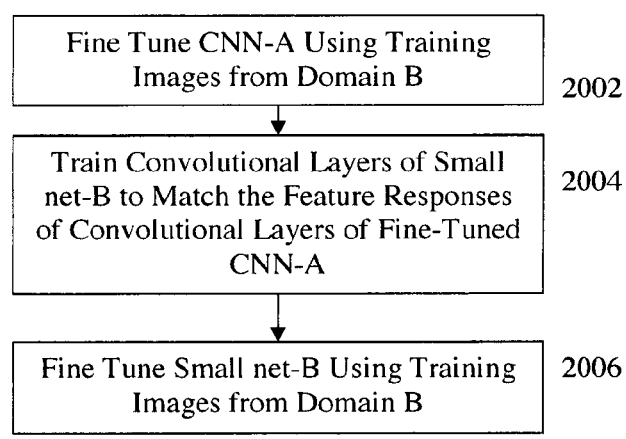
FIG. 20 illustrates a method for training a CNN using feature-level supervision transfer learning according to an embodiment of the present invention.
Figure 21A:
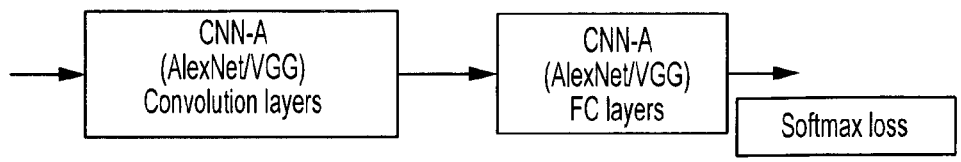
FIGS. 21A, 21B, and 21C illustrate method steps of the method of FIG. 20 using the framework illustrated in FIG. 19.
Figure 21B:
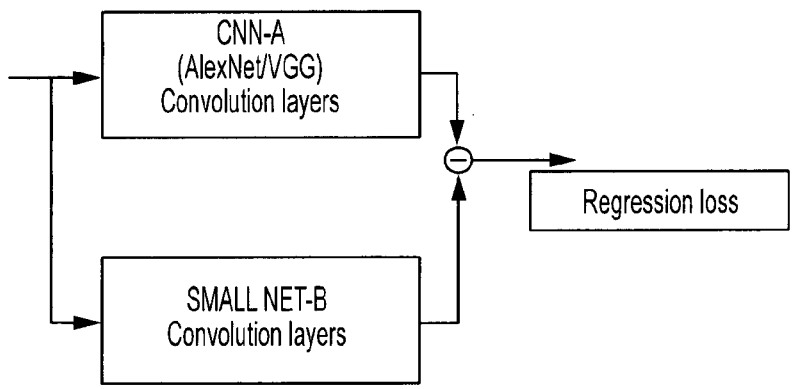
Figure 21C:
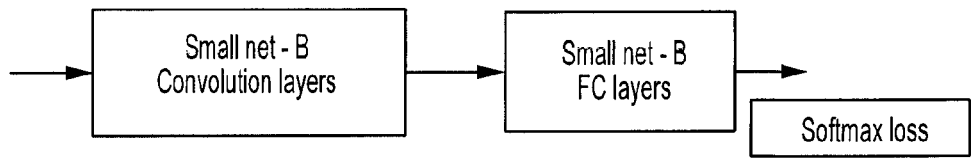

FIG. 20 illustrates a method for training a CNN using feature-level supervision transfer learning according to an embodiment of the present invention. FIGS. 21A, 21B, and 21C illustrate method steps of the method of FIG. 20 using the framework illustrated in FIG. 19. In particular, FIGS. 21A, 21B, and 21C decompose the feature-level supervision transfer learning framework of FIG. 19 into steps corresponding to steps 2002, 2004, and 2006 of FIG. 20 respectively.

Referring to FIG. 20, at step 2002, CNN-A is fine-tuned using training images from domain B. It is assumed in the method of FIG. 20 that the first CNN (CNN-A) is an already existing well-trained network trained based on a large number of training images from domain A. In step 2002, CNN-A is fine-tuned by retraining CNN-A using the smaller-size database of medical images from domain B as training images, with the previously trained weights of CNN-A used for initialization. FIG. 21A illustrates fine-tuning CNN-A in an exemplary embodiment. As shown in FIG. 21A, both the convolution layers and the FC layers of CNN-A are re-trained based on the training images from domain B. As shown in FIG. 21A, the re-training (fine-tuning) of CNN-A can use a softmax loss to tune the weights of the convolution layers and the FC layers of CNN-A based on the training images from domain B.

At step 2004, convolution layers of Small net-B are trained to match the feature responses from the convolutional layers of the finely-tuned CNN-A. This step performs the feature level supervision (FLS), as it initially trains the convolutional layers of Small net-B, which may have less convolutional layers and/or weights than CNN-A to approximate the output of the convolutional layers of CNN-A after CNN-A has been finely tuned for domain B. FIG. 21B illustrates this step of training the convolutional layers of Small net-B to match the feature responses from the convolutional layers of the finely-tuned CNN-A in an exemplary embodiment. As shown in FIG. 21B, a regression loss can be used to learn weights for the convolutional layers of Small net-B to best match the output (feature responses) from the convolutional layers of the finely-tuned CNN-A.

At step 2006, Small net-B is finely tuned using training images from domain B. This step trains both the convolution layers and the FC layers of Small net-B based on the training images from domain B. This results in tuning the weights for the convolutional layers of Small net-B that were initialized in step 2004 and learning weights for the FC layers of Small net-B, in order to learn an optimal mapping from the training images in domain B to the ground truth final outcomes (e.g., classification result, segmentation result, etc.) for the training images. FIG. 21C illustrates this step of fine tuning Small net-B in an exemplary embodiment. As shown in FIG. 21C, a softmax loss can be used to learn the weights for the convolutional layers and the FC layers of Small net-B based on the training images in domain B. Once the training of Small net-B is complete, Small net-B can be stored, for example of a storage device or memory of a computer system, and used to perform the medical image analysis task (e.g., classification, segmentation, etc.) for unseen images in domain B.

The above described feature level supervision transfer learning method was tested on a challenging problem of classifying an ultrasound abdominal image into one of 11 views, namely Liver Left Transverse, Liver Left Longitudinal, Liver Right Transverse, Liver Right Longitudinal, Kidney Left Transverse, Kidney Left Longitudinal, Kidney Right Transverse, Kidney Right Longitudinal, Spleen Transverse, Spleen Longitudinal, and None-of-the-above. The training set after data augmentation contained a total of 131,003 images, with about 10,000 images per view. The test set after data augmentation contained 56,213 images. Table 4, below, presents the classification accuracy of various methods for comparison. The small Net-B transfer-learned from AlexNet-A is more than six times smaller than the original AlexNet-A yet it has a slightly better performance than the fined-tuned AlexNet-A, which is much better than the AlexNet-A trained from scratch. One experimental variant ('16c') is as follows: when training, a 16-view classifier can be trained, as the none-of-the above can be further subdivided into 6 classes but still output the final label as one of the 11 views. Using this variant, the classification accuracy is improved by about 1% with a small increase in terms of the number of model parameters. The same experiments were then repeated using the VGG-A net, which obtained better accuracy than those models transferred from the AlexNet-A. Finally, using SmallNet4-B, which is transferred from VGGNet-A using FLS, we aggregate all features from all intermediate layers and then perform feature selection before feeding a SVM for final view classification. This turned out the most accurate solution, achieving an accuracy of 86.22%.

TABLE 4

| Network | Accuracy (%) | #Params (M) | CPU (ms) |
|---|---|---|---|
| AlexNet-A, fine-tune, 11c | 79.97 | 61M | 102 |
| AlexNet-A, from scratch, 11c | 74.93 | 61M | 102 |
| SmallNet-B, AlexNet FLS, 11c | 80.11 | 10M | 17 |
| SmallNet-B, from scratch, 11c | 75.71 | 10M | 17 |
| AlexNet-A, fine-tune, 16c | 80.06 | 61M | 102 |
| SmallNet-B, AlexNet FLS, 16c | 81.01 | 11M | 29.37 |
| VGGNet-A, fine-tune, 11c | 82.99 | 138M | 1568 |
| SmallNet3-B, VGGNet FLS, 16c | 82.40 | 27M | 131 |
| VGGNet-A, fine-tune, 16c | 85.61 | 138M | 1568 |
| SmallNet4-B, VGGNet FLS, 16c | 85.02 | 27M | 131 |
| SmallNet4-B, VGGNet FLS, 16c, Feature selection | 86.22 | 27M | |

Figure 22:
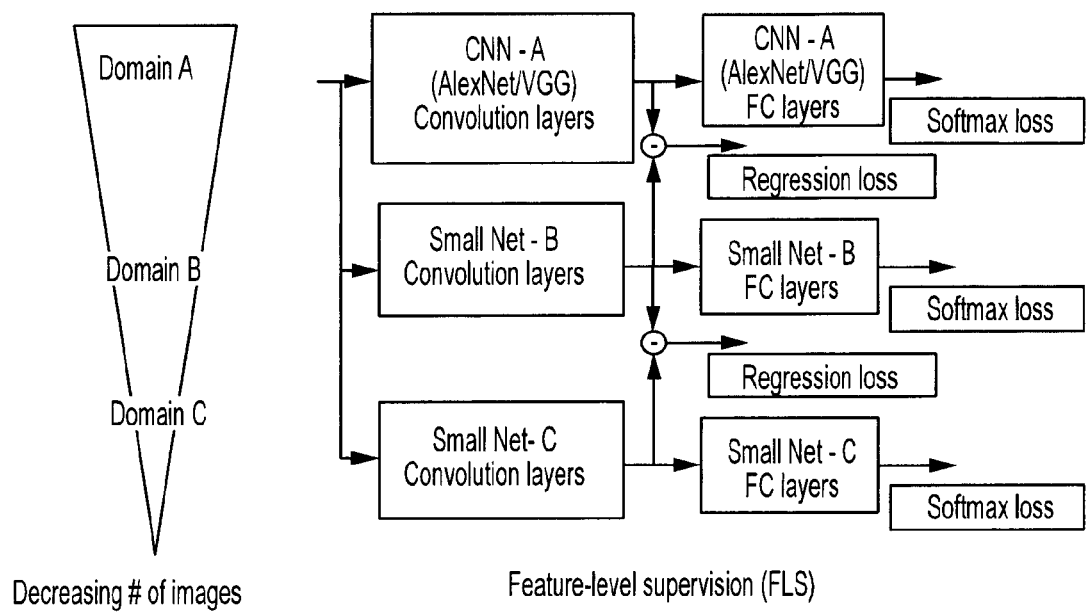
FIG. 22 illustrates a framework for feature level supervision transfer learning across a hierarchy of domains according to an embodiment of the present invention.

FIG. 22 illustrates a framework for feature level supervision transfer learning across a hierarchy of domains according to an embodiment of the present invention. As shown in FIG. 22, feature level supervision transfer learning can be applied across a hierarchy of domains (A, B, C) with decreasing number of medical images available in each subsequent domain. Starting with an already trained CNN-A trained from a large number of training images in domain A, the feature level supervision transfer learning method described above is applied to train Small net-B for domain B from CNN-A. The feature level supervision transfer learning method described above is then performed again to train another CNN (Small net-C) for domain C from Small net-B. This can also be repeated for additional domains in a hierarchy of domains with decreasing numbers of images.

Applying feature level supervision (FLS) transfer learning across a hierarchy of domains works better, as compared with fine-tuning transfer learning. This is verified by experiments performed on classifying an ultrasound thyroid image into 5 views, namely isthmus, left thyroid transverse, left thyroid longitudinal, right thyroid transverse, and right thyroid longitudinal. This experiment utilized a total of 549 training images and 143 test images. Table 5 shows the classification accuracy of various methods. Fine-turning VGGNet-A directly to domain-C (the thyroid domain) yields an accuracy of 74.13%. Fine-tuning the VGNet-A first to domain-B (the abdominal domain) and the further fine tuning to domain-C gives an accuracy of 74.82%, only a slight improvement. Using the FLS transfer learning and performing it across three domains (first from domain-A to domain-B, and then to domain-C) records a correct classification 81.12% of time. Finally, further performing feature aggregation and selection and feeding the selected features into a SVM gives the highest accuracy of 86.71%.

TABLE 5

| METHOD | ACCURACY |
|---|---|
| Fine-Tune VGGNet | 74.1259 |
| 2-time Fine-tune, VGGNet | 74.8252 |
| 2-time FLS supervision VGG Net | 81.1189 |
| 2-time FLS supervision VGG Net, Feature Selection | 86.71 |

Feature Channel Filtering in a Convolutional Neural Network

The convolutional neural network (CNN) is an effective deep learning architecture that is used in many medical image analysis applications, including for medical image segmentation, as well as other medical image analysis tasks. However, deep neural networks, such as CNNs, may be computationally expensive and take significant processing time to implement. This embodiment provides a method for approximating a CNN using feature channel filtering to reduce the parameters required to represent the trained CNN model and improve computational efficiency. The method described herein can be used for approximating a CNN in used in any of the above described segmentation methods. The method described herein can also be used for other medical image analysis tasks that utilize a CNN as well.

The CNN endows a hierarchical architecture including multiple layers. The inputs to a layer are a set of feature channels (or feature maps) and the outputs are another set of feature maps. CNN architectures stack multiple convolutional layers for feature extraction. Suppose that the input feature channels (or maps), each channel being any N-dimensional image, are denoted by $\{I(x_1, x_2, \ldots, x_N, c); c=1:C\}$ that for a (N+1)D tensor, and the output feature channels are denoted by $\{J(x_1, x_2, \ldots, x_N, d); d=1:D\}$. We have:

$$J(x_1,x_2,\ldots,x_N,d)=\sigma-[\Sigma_{m_1=-w_1:w_1}\Sigma_{m_2=-w_2:w_2}\cdots \Sigma_{c=1:C} I(x_1,x_2,\ldots,x_N,c)g(m_1,m_2,\ldots m_N,c,d)], \quad (4)$$

where $\{g(m_1, m_2, \ldots m_N, c, d); m_1=-w_1:w_1, \ldots c=1:C\}$ is the set of filters (or kernels) of size $(2w_1+1)^* \ldots *(2w_N+1)$ for the dth output feature channel and $\sigma[\cdot]$ Is the nonlinear activation function, such as a sigmoid function or ReLU function. In the above, it is assumed that there is no pooling between layers, without loss of generality. The operations in Equation (4) are convolutional in the spatial dimensions for each feature channel, but exhaustive in the feature channel dimension (i.e., all feature channels are used). The exhaustive nature of the feature channel dimension renders computational inefficiency and possible performance deficiency. The total number of parameters for a convolutional layer is $C^*D^*(2w_1+1)^* \ldots *(2w_N+1)$.

Figure 23:
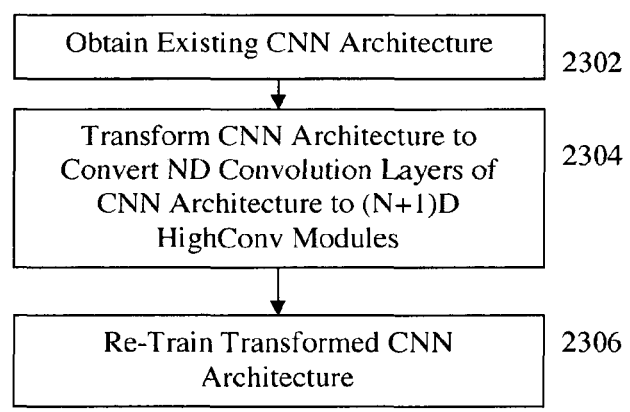
FIG. 23 illustrates a method for approximating a CNN architecture using feature channel filtering according to an embodiment of the present invention.

FIG. 23 illustrates a method for approximating a CNN architecture using feature channel filtering according to an embodiment of the present invention. Referring to FIG. 23, at step 2302, an existing CNN architecture for an N-dimensional domain is obtained. For example, a CNN architecture can be trained for a specific task (e.g., segmentation) from training medical image datasets or an already trained CNN architecture can be loaded.

At step 2304, the existing CNN architecture is transformed by converting the N-dimensional convolutional layers to (N+1)-dimensional high-convolutional ("HighConv") modules. According to an advantageous embodiment, for a particular convolutional layer, meaningful kernels are learned in the incoming channel space. This process is represented as a convolution in the channel space. In other words, convolutions or filtering are performed to the input feature channels to learn features not only in the spatial domain of each feature channel, but also in the feature channel space. This is referred to herein as "feature channel filtering". The benefit of the feature channel filtering is that, as opposed to the convolutions that convolve over all incoming feature channels, feature channel filtering reduces the number of feature channels needed and thus reduces the number of parameters required to represent the trained model, which improves computational efficiency. Applying the feature channel filtering on a convolutional layer results in a transformed layer referred to herein as a HighConv module (or HighConv block).

In terms a parameters, consider a 2D convolutional layer with k filters and C channels with (W, H) spatial filters. The number of parameters for this 2D convolutional layer is #params=C*D*W*H. The number of parameters for a HighConv block that replaces the 2D convolutional layer using feature channel filtering is #params=C*1*d*W*H. Therefore, the HighConv block saves computations given that d<D, where d is a tuning parameter that determines the channel space kernel size. This brings a computational savings of D/d times for this layer. The feature channel filtering can be similarly applied to each convolutional layer of the existing CNN architecture. The feature channel filter can be applied independently or in conjunction with other approximation techniques (e.g., decomposed network, etc.) for each layer.

Figure 24:
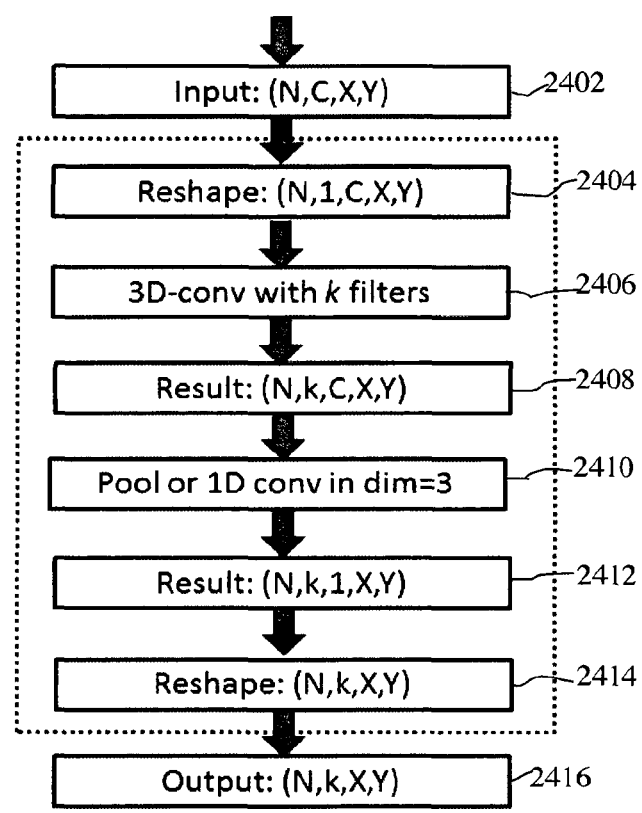
FIG. 24 illustrates an exemplary HighConv module that inputs 2D images according to an embodiment of the present invention.

FIG. 24 illustrates an exemplary HighConv module that inputs 2D images according to an embodiment of the present invention. As shown in FIG. 4, the input 2402 to the HighConv module has parameters of (N, C, X, Y), where N is the batch size, C is the number of input channels, and X, Y are the feature map spatial dimensions. The input is reshaped (2404) with parameters (N, 1, C, X, Y) and then 3D convolution is performed with k filters (2406), which results in parameters of (N, k, C, X, Y) (2408). Pooling or 1D convolution is performed in the third dimension (i.e., the feature channel space) (2410), resulting in parameters of (N,k,1,X,Y) (2412), which are reshaped (2414) as (N,k,X, Y). The output (2416) of the HighConv module has parameters (N,k,X,Y).

Returning to FIG. 23, at step 2306, the transformed CNN architecture is re-trained. In particular, the transformed CNN architecture was HighConv modules can be re-trained with the same training data, same optimizer, etc., used to train the original CNN architecture. Given the smaller network architecture to carry on the same task as the original CNN architecture, the model is forced to learn a better representation for the problem, which implicitly acts as a "regularizer" and potentially leads to better learning. Such learning implicitly makes the network deeper, potentially leading to better representational power with more non-linear operations.

Figure 25:
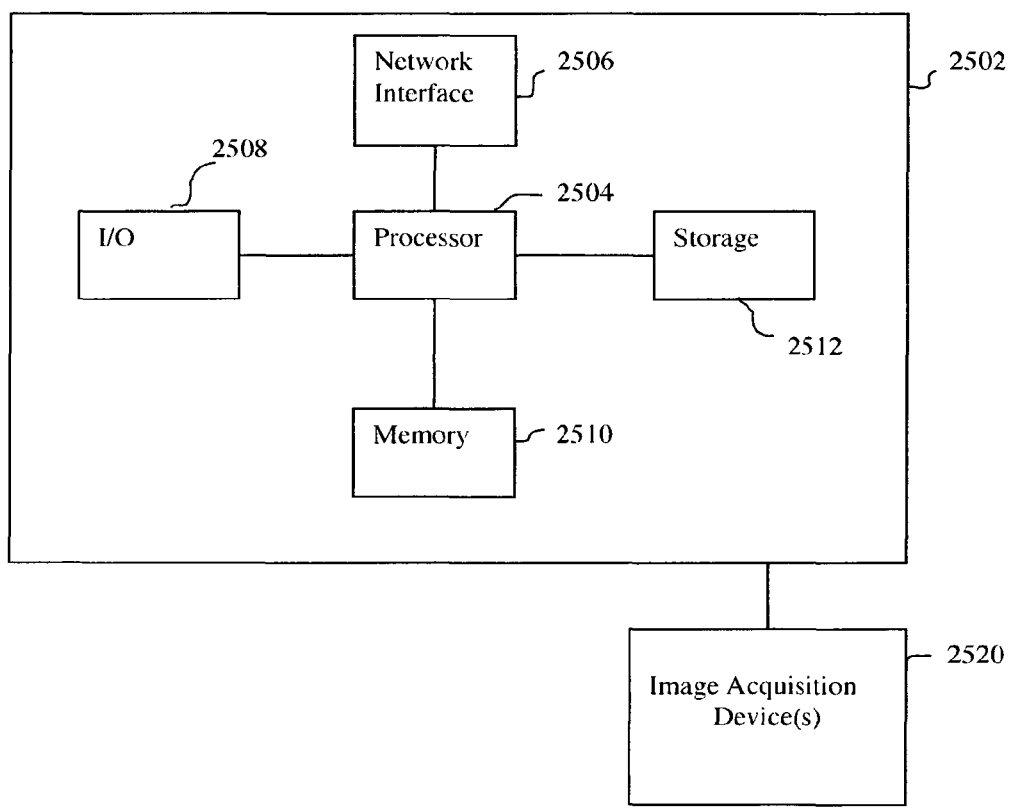
FIG. 25 is a high-level block diagram of a computer capable of implementing the present invention.

The above-described methods for artificial intelligence based medical image segmentation and training deep network architectures for medical image segmentation can be implemented on one or more computers using well-known computer processors, memory units, storage devices, computer software, and other components. A high-level block diagram of such a computer is illustrated in FIG. 25. Computer 2502 contains a processor 2504, which controls the overall operation of the computer 2502 by executing computer program instructions which define such operation. The computer program instructions may be stored in a storage device 2512 (e.g., magnetic disk) and loaded into memory 2510 when execution of the computer program instructions is desired. Thus, the method steps illustrated in FIGS. 2, 3, 5, 7, 9, 12, 13, 16, 19, 20, 21A-21C, 22, 23, and 24 may be defined by the computer program instructions stored in the memory 2510 and/or storage 2512 and controlled by the processor 2504 executing the computer program instructions. One or more image acquisition devices 2520, such as a CT scanning device, C-arm image acquisition device, MR scanning device, Ultrasound device, etc., can be connected to the computer 2502 to input image data to the computer 2502. It is possible that the computer and one or more of the image acquisition devices 2520 may be implemented as one device. It is also possible that the image acquisition devices 2520 and the computer 2502 communicate wirelessly through a network or wireless communication protocol. In a possible embodiment, the computer 2502 may be located remotely with respect to the image acquisition devices 2520 and may perform some or all of the method steps of FIGS. 2, 3, 5, 7, 9, 12, 13, 16, 19, 20, 21A-21C, 22, 23, and 24 as part of a server or cloud based service. The computer 2502 also includes one or more network interfaces 2506 for communicating with other devices via a network. The computer 2502 also includes other input/output devices 2508 that enable user interaction with the computer 2502 (e.g., display, keyboard, mouse, speakers, buttons, etc.). One skilled in the art will recognize that an implementation of an actual computer could contain other components as well, and that FIG. 25 is a high level representation of some of the components of such a computer for illustrative purposes.

The above described methods for artificial intelligence based medical image segmentation and/or training deep neural networks may be implemented in network-based cloud computing system. In such a network-based cloud computing system, a server communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. Certain steps of the above described methods may be performed by a server or by other computers/processors in the network-based cloud-computing system. Certain steps of the above described methods may be performed locally by a client computer in a network-based cloud computing system. The steps of the above described methods for artificial intelligence based medical image segmentation and/or training deep neural networks may be implemented in network-based cloud computing system may be performed by the network-based cloud-computing system or by a local client computer in any combination.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for autonomous artificial intelligence based medical image segmentation, comprising:
    receiving a medical image of a patient;
    automatically determining a current segmentation context based on the medical image by inputting the medical image to a trained deep neural network that automatically extracts learned image characteristics from the medical image;
    automatically selecting at least one segmentation algorithm from a plurality of segmentation algorithms including a plurality of different deep-learning based segmentation algorithms based on the current segmentation context using the trained deep neural network, wherein the trained deep neural network predicts a best segmentation algorithm or combination of segmentation algorithms from the plurality of segmentation algorithms for performing segmentation of a target anatomical structure in the medical image based on the extracted learned image characteristics; and
    segmenting the target anatomical structure in the medical image using the selected at least one segmentation algorithm.

2. The method of claim 1, wherein the steps of automatically determining the current segmentation context based on the medical image and selecting the at least one segmentation algorithm from the plurality of segmentation algorithms based on the current segmentation context are performed by a software-based trained master segmentation artificial agent running on a computer system.

3. The method of claim 1, wherein automatically determining a current segmentation context based on the medical image further comprises:
    automatically identifying the target anatomical structure based on a view of the medical image currently being visualized on a display device by automatically detecting what anatomical structure is currently being visualized on the display device using a trained machine learning based classifier.

4. The method of claim 3, wherein automatically selecting at least one segmentation algorithm from a plurality of segmentation algorithms comprises:
    automatically selecting, by the trained deep neural network, the at least one segmentation algorithm from multiple segmentation algorithms specialized for segmentation of the automatically identified target anatomical structure based on the extracted learned image characteristics.

5. The method of claim 1, wherein the trained deep neural network is trained based on medical image training samples and synthetic training samples generated at a plurality if noise levels from the medical image training samples.

6. The method of claim 1, wherein automatically selecting at least one segmentation algorithm from a plurality of segmentation algorithms comprises selecting multiple segmentation algorithms from the plurality of segmentation algorithms based on the current segmentation context, and segmenting the target anatomical structure in the medical image using the selected at least one segmentation algorithm comprises:
    segmenting the target anatomical structure in the medical image using each of the selected multiple segmentation algorithms; and
    fusing segmentation results from the selected multiple segmentation algorithms to generate final segmentation result for the target anatomical structure in the medical image.

7. The method of claim 1, wherein the plurality of different deep-learning based segmentation algorithms each have a respective deep network architecture trained for a specific segmentation task.

8. The method of claim 1, wherein segmenting the target anatomical structure in the medical image using the selected at least one segmentation algorithm comprises:
    segmenting the target anatomical structure in the medical image using the trained deep neural network with one or more integrated priors.

9. The method of claim 1, wherein the selected at least one segmentation algorithm comprises a deep reinforcement learning based segmentation algorithm, and segmenting the target anatomical structure in the medical image using the selected at least one segmentation algorithm comprises:

iteratively adjusting a statistical shape model representing a shape of the target anatomical structure in the medical image by selecting, at each iteration, an action corresponding to an adjustment of a parameter of the statistical shape model based on action values calculated using deep neural network trained using deep reinforcement learning.

10. The method of claim 1, wherein segmenting the target anatomical structure in the medical image using the selected at least one segmentation algorithm comprises:

generating a plurality of Gaussian distributed probability maps at different scales from the medical image using a trained deep image-to-image network;

combining the plurality of Gaussian probability maps at the different scales into a combined probability map; and extracting a segmented boundary of the target anatomical structure from the medical image based on the combined probability map.

11. The method of claim 1, wherein the selected at least one segmentation algorithm comprises a deep learning partial inference based segmentation algorithm, and segmenting the target anatomical structure in the medical image using the selected at least one segmentation algorithm comprises:

generating an initial segmentation mask for the target anatomical structure from the medical image using a trained initial convolutional encoder decoder (CED);

constructing a unified tensor combining a current segmentation mask and the medical image; and generating an updated segmentation mask for the target anatomical structure using a trained partial inference CED.

12. The method of claim 1, wherein segmenting the target anatomical structure in the medical image using the selected at least one segmentation algorithm comprises:

fitting an active shape model to a shape of the target anatomical structure in the medical image by using a recurrent neural network (RNN) to adjust locations of points on the active shape model.

13. An apparatus for autonomous artificial intelligence based medical image segmentation, comprising:

means for receiving a medical image of a patient;

means for automatically determining a current segmentation context based on the medical image by inputting the medical image to a trained deep neural network that automatically extracts learned image characteristics from the medical image;

means for automatically selecting at least one segmentation algorithm from a plurality of segmentation algorithms including a plurality of different deep-learning based segmentation algorithms based on the current segmentation context using the trained deep neural network, wherein the trained deep neural network predicts a best segmentation algorithm or combination of segmentation algorithms from the plurality of segmentation algorithms for performing segmentation of a target anatomical structure in the medical image based on the extracted learned image characteristics; and means for segmenting the target anatomical structure in the medical image using the selected at least one segmentation algorithm.

14. The apparatus of claim 13, wherein the means for automatically determining a current segmentation context based on the medical image further comprises:

means for automatically identifying the target anatomical structure based on a view of the medical image currently being visualized on a display device by automatically detecting what anatomical structure is currently being visualized on the display device using a trained machine learning based classifier.

15. The apparatus of claim 14, wherein the means for automatically selecting at least one segmentation algorithm from a plurality of segmentation algorithms comprises:

means for automatically selecting, by the trained deep neural network, the at least one segmentation algorithm from multiple segmentation algorithms specialized for segmentation of the automatically identified target anatomical structure based on the extracted learned image characteristics.

16. The apparatus of claim 13, wherein the means for automatically selecting at least one segmentation algorithm from a plurality of segmentation algorithms comprises means for selecting multiple segmentation algorithms from the plurality of segmentation algorithms based on the current segmentation context, and the means for segmenting the target anatomical structure in the medical image using the selected at least one segmentation algorithm comprises:

means for segmenting the target anatomical structure in the medical image using each of the selected multiple segmentation algorithms; and means for fusing segmentation results from the selected multiple segmentation algorithms to generate final segmentation result for the target anatomical structure in the medical image.

17. A non-transitory computer readable medium storing computer program instructions for autonomous artificial intelligence based medical image segmentation, the computer program instructions when executed by a processor perform operations comprising:

receiving a medical image of a patient;

automatically determining a current segmentation context based on the medical image by inputting the medical image to a trained deep neural network that automatically extracts learned image characteristics from the medical image;

automatically selecting at least one segmentation algorithm from a plurality of segmentation algorithms including a plurality of different deep-learning based segmentation algorithms based on the current segmentation context using the trained deep neural network, wherein the trained deep neural network predicts a best segmentation algorithm or combination of segmentation algorithms from the plurality of segmentation algorithms for performing segmentation of a target anatomical structure in the medical image based on the extracted learned image characteristics; and segmenting the target anatomical structure in the medical image using the selected at least one segmentation algorithm.

18. The non-transitory computer readable medium of claim 17, wherein automatically determining a current segmentation context based on the medical image further comprises:

automatically identifying the target anatomical structure based on a view of the medical image currently being visualized on a display device by automatically detecting what anatomical structure is currently being visualized on the display device using a trained machine learning based classifier.

19. The non-transitory computer readable medium of claim 18, wherein automatically selecting at least one segmentation algorithm from a plurality of segmentation algorithms comprises:
   automatically selecting, by the trained deep neural network, the at least one segmentation algorithm from multiple segmentation algorithms specialized for segmentation of the automatically identified target anatomical structure based on the extracted learned image characteristics.

20. The non-transitory computer readable medium of claim 17, wherein automatically selecting at least one segmentation algorithm from a plurality of segmentation algorithms comprises selecting multiple segmentation algorithms from the plurality of segmentation algorithms based on the current segmentation context, and segmenting the target anatomical structure in the medical image using the selected at least one segmentation algorithm comprises:
   segmenting the target anatomical structure in the medical image using each of the selected multiple segmentation algorithms; and
   fusing segmentation results from the selected multiple segmentation algorithms to generate final segmentation result for the target anatomical structure in the medical image.

21. The non-transitory computer readable medium of claim 17, wherein the plurality of different deep-learning based segmentation algorithms each have a respective deep network architecture trained for a specific segmentation task.

* * * * *